(12) United States Patent
Potyrailo

(10) Patent No.: US 12,313,580 B2
(45) Date of Patent: May 27, 2025

(54) SYSTEM AND METHOD FOR GAS SENSOR THAT CORRECTS FOR SENSOR POISON LEVEL

(71) Applicant: General Electric Company, Schenectady, NY (US)

(72) Inventor: Radislav Alexandrovich Potyrailo, Niskayuna, NY (US)

(73) Assignee: GE Infrastructure Technology LLC, Greenville, SC (US)

( * ) Notice: Subject to any disclaimer, the term of this patent is extended or adjusted under 35 U.S.C. 154(b) by 371 days.

(21) Appl. No.: 17/859,907

(22) Filed: Jul. 7, 2022

(65) Prior Publication Data

US 2024/0013647 A1    Jan. 11, 2024

(51) Int. Cl.
*G01N 27/12* (2006.01)
*G01N 27/416* (2006.01)
*G01N 33/00* (2006.01)

(52) U.S. Cl.
CPC ....... *G01N 27/125* (2013.01); *G01N 27/4163* (2013.01); *G01N 33/0063* (2013.01)

(58) Field of Classification Search
CPC ............. G01N 27/125; G01N 27/4163; G01N 33/0063
See application file for complete search history.

(56) References Cited

U.S. PATENT DOCUMENTS

| | | | |
|---|---|---|---|
| 7,849,727 B2 | 12/2010 | Gardner et al. | |
| 8,773,138 B2 | 7/2014 | Shinada et al. | |
| 9,618,491 B1 * | 4/2017 | Kellaway | G01N 33/0031 |
| 10,368,146 B2 | 7/2019 | Potyrailo et al. | |
| 10,812,878 B2 | 10/2020 | Potyrailo et al. | |
| 10,996,210 B2 | 5/2021 | Potyrailo et al. | |
| 2002/0168772 A1 | 11/2002 | Lloyd et al. | |
| 2016/0187279 A1 | 6/2016 | Tayebi et al. | |
| 2018/0231485 A1 * | 8/2018 | Potyrailo | G01N 33/0047 |
| 2019/0204291 A1 | 7/2019 | Potyrailo et al. | |
| 2020/0386701 A1 * | 12/2020 | Potyrailo | G01N 27/122 |
| 2020/0386728 A1 | 12/2020 | Potyrailo | |

(Continued)

OTHER PUBLICATIONS

Schüler et al., Metal oxide semiconductor gas sensor self-test using Fourier-based impedance spectroscopy, Journal of Sensors and Sensor Systems, vol. 3, Sep. 25, 2014, p. 280-289.

(Continued)

*Primary Examiner* — Ryan D Walsh
(74) *Attorney, Agent, or Firm* — Fletcher Yoder, P.C.

(57) ABSTRACT

A system and a method for gas sensing while correcting for a poison level of a gas sensor. The gas sensor provides first dielectric excitation of the gas sensing material at a first set of frequencies, measures responses of the gas sensing material to the first dielectric excitation while the gas sensing material is in contact with the fluid sample, provides second dielectric excitation of the gas sensing material at a second set of frequencies, measures responses of the gas sensing material to the second dielectric excitation while the gas sensing material is in contact with the fluid sample, and determines, based on the responses of the gas sensing material to the first and second dielectric excitation, identities, respective concentrations, or a combination thereof, of at least one analyte gas in a fluid sample, and a sensor poison level of the gas sensing material.

20 Claims, 10 Drawing Sheets

(56) References Cited

U.S. PATENT DOCUMENTS

| | | | |
|---|---|---|---|
| 2021/0072175 A1 | 3/2021 | Potyrailo et al. | |
| 2021/0109049 A1 | 4/2021 | Potyrailo | |
| 2021/0278384 A1* | 9/2021 | Potyrailo | ........... G01N 33/0031 |
| 2024/0011900 A1* | 1/2024 | Potyrailo | ........... G01N 33/0006 |
| 2024/0011928 A1* | 1/2024 | Potyrailo | ................. H05B 3/02 |
| 2024/0011930 A1* | 1/2024 | Potyrailo | ............. G01N 27/223 |
| 2024/0011934 A1* | 1/2024 | Potyrailo | ............. G01N 27/404 |
| 2024/0011962 A1* | 1/2024 | Potyrailo | ........... G01N 33/0016 |
| 2024/0133837 A1* | 4/2024 | Potyrailo | ............. G01N 27/228 |
| 2024/0295518 A1* | 9/2024 | Potyrailo | ............. G01N 27/026 |
| 2024/0295536 A1* | 9/2024 | Potyrailo | ............... G01N 27/27 |

OTHER PUBLICATIONS

Potyrailo et al., Extraordinary performance of semiconducting metal oxide gas sensors using dielectric excitation, Nature Electronics, vol. 3, p. 280-289, May 2020.

Potyrailo et al., Multi-gas sensors based on dielectric excitation, GE Research, https://www.ge.com/research/project/multi-gas-sensors-based-dielectric-excitation, accessed Aug. 12, 2020.

Jong-Heun Lee, Linear gas sensing with dielectric excitation, Nature Electronics, May 2020.

Schüler, M.; Sauerwald, T.; Schütze, A., A novel approach for detecting HMDSO poisoning of metal oxide gas sensors and improving their stability by temperature cycled operation, J. Sens. Sens. Syst. 2015, 4, (2), 305-311.

Schüler, M. et al., Impedance based detection of HMDSO poisoning in metal oxide gas sensors, Tech. Mess. 2017, 84, (11), 697-705.

Potyrailo, R. A., Multivariable sensors for ubiquitous monitoring of gases in the era of Internet of Things and Industrial Internet, Chem. Rev. 2016, 116, 11877-11923.

Jeong, S. Y.; Kim, J. S.; Lee, J. H., Rational Design of Semiconductor-Based Chemiresistors and their Libraries for Next-Generation Artificial Olfaction, Adv. Mater. 2020, 2002075.

Schultealbert, C.; Uzun, I.; Baur, T.; Sauerwald, T.; Schütze, A., Siloxane treatment of metal oxide semiconductor gas sensors in temperature-cycled operation—sensitivity and selectivity, J. Sens. Sens. Syst. 2020, 9, (2), 283-292.

Schultealbert, C.; Baur, T.; Sauerwald, T.; Schütze, A., Compensation of siloxane poisoning of metal oxide semi-conductor gas sensors in temperature cycled operation, SMSI 2020—Sensors and Instrumentation 2020, 197-198.

Weimar, U.; Göpel, W., AC Measurements on Tin Oxide Sensors to Improve Selectivities and Sensitivities, Sens. Actuators B 1995, 26, 13-18.

Simon, U.; Sanders, D.; Jockel, J.; Brinz, T., Setup for High-Throughput Impedance Screening of Gas-Sensing Materials, J. Comb. Chem. 2005, 7, 682-687.

Schipani, F.; Miller, D.; Ponce, M.; Aldao, C.; Akbar, S.; Morris, P., Electrical Characterization of Semiconductor Oxide-Based Gas Sensors Using Impedance Spectroscopy: A Review, Rev. Adv. Sci. Eng. 2016, 5, 86-105.

Gutierrez, J.; Ares, L.; Horillo, M.; Sayago, I.; Agapito, J.; Lopez, L., Use of complex impedance spectroscopy in chemical sensor characterization, Sens. Actuators B 1991, 4, (3-4), 359-363.

Barsan, N.; Weimar, U., Understanding the fundamental principles of metal oxide based gas sensors; the example of CO sensing with $SnO_2$ sensors in the presence of humidity, J. Phys.: Condens. Matter 2003, 15, R813-R839.

Pokhrel, S.; Simion, C.; Quemener, V.; Barsan, N.; Weimar, U., Investigations of conduction mechanism in $Cr_2O_3$ gas sensing thick films by ac impedance spectroscopy and work function changes measurements, Sens. Actuators B 2008, 133, (1), 78-83.

Schipani, F.; Miller, D. R.; Ponce, M. A.; Aldao, C. M.; Akbar, S. A.; Morris, P. A.; Xu, J. C., Conduction mechanisms in $SnO_2$ single-nanowire gas sensors: An impedance spectroscopy study, Sens. Actuators B 2017, 241, 99-108.

Hikita, K.; Miyayama, M.; Yanagida, H., New Gas-Sensing Method for Detecting Carbon Monoxide by Use of the Complex Impedance of a CuO/ZnO Heterocontact under a dc Bias Voltage, J. Am. Ceram. Soc. 1994, 77, (7), 1961-1964.

Göpel, W .; Schierbaum, K. D., $SnO_2$ sensors: current status and future prospects, Sens. Actuators B 1995, 26-27, 1-12.

Rheaume, J. M.; Pisano, A. P., A review of recent progress in sensing of gas concentration by impedance change, Ionics 2011, 17, 99-108.

* cited by examiner

SYSTEM AND METHOD FOR GAS SENSOR THAT CORRECTS FOR SENSOR POISON LEVEL

BACKGROUND

The subject matter disclosed herein generally relates to gas sensing, and more specifically relates to gas sensing using metal oxide semiconductor (MOS) sensors.

Metal oxide semiconductor (MOS) sensors can be operated as chemiresistors and are popular because of their ability to detect numerous gases with the proper selection of the base semiconductor material and doping materials. In such gas-responsive chemiresistors, a change in resistance of the MOS sensing material is measured. The change in resistance of the MOS sensing material is proportional to the gas concentrations in a fluid sample, as determined based on the non-linear power law relation between the gas concentration and the change in the resistance of the MOS sensing material. However, exposure to certain gases (e.g., siloxane vapor) can irreversibly alter the response of the MOS sensing material to known gases, such that the sensor loses its initial ability to respond to the gas concentrations. This is sometimes referred to as "poisoning" of a sensor. Accordingly, it may be desirable to develop a way to correct for effects of poisoning of MOS sensors.

BRIEF DESCRIPTION

With the foregoing in mind, present embodiments are directed to a system and a method for sensing of at least one gas using dielectric excitation, in which a poison level of the sensor is determined and accounted for. Contrary to conventional gas sensor designs, embodiments of the gas sensor disclosed herein utilize techniques for determining the poison level of the gas sensor and then correct measured responses of the sensor to dielectric excitation, based on the determined poison level, and to determine an identity and/or concentration of at least one gas present in a fluid sample. The disclosed gas sensors and gas sensing methods unexpectedly provide desirable characteristics, such as increased lifespan in environments that may contain sensor-poisoning materials.

For example, in an embodiment, a gas sensor for analysis of one or more gases in a fluid sample includes a gas sensing material and a measurement circuit. The gas sensing material is configured to contact the fluid sample. The measurement circuit is operatively coupled to the gas sensing material and configured to provide first and second dielectric excitation of the gas sensing material at first and second respective sets of frequencies, measure responses of the gas sensing material to the first and second dielectric excitation at the first and second respective sets of frequencies while the gas sensing material is in contact with the fluid sample, and provide, based on the responses of the gas sensing material to the first and second dielectric excitation at the first and second respective sets of frequencies, correction for a poison level of the gas sensing material.

In another embodiment, a method of operating a gas sensor includes exposing the gas sensing material of the gas sensor to a fluid sample, providing, via a measurement circuit operatively coupled to the gas sensing material, first dielectric excitation of the gas sensing material at a first set of frequencies, measuring responses of the gas sensing material to the first dielectric excitation at the first set of frequencies while the gas sensing material is in contact with the fluid sample, providing, via the measurement circuit, second dielectric excitation of the gas sensing material at a second set of frequencies, measuring responses of the gas sensing material to the second dielectric excitation at the second set of frequencies while the gas sensing material is in contact with the fluid sample, and determining, based on the responses of the gas sensing material to the first and second dielectric excitation at the second set of frequencies, identities, respective concentrations, or a combination thereof, of at least one analyte gas in the fluid sample, and a poison level of the gas sensing material.

In a further embodiment, a method of calibrating a gas sensor includes obtaining first responses of the gas sensor to first dielectric excitation at a first frequency range while the gas sensor is in contact with the a range of known concentrations of a gas, wherein the first responses of the gas sensor over the range of known concentrations of the gas are substantially linear, relating the first responses of the sensor to the range of known concentrations of the gas, computing one or more analytical fit coefficients between the first responses and the range of known concentrations of the gas, wherein the one or more analytical fit coefficients correct for a poison level of the gas sensor, storing the one or more analytical fit coefficients on an on-board memory, accessible by an on-board processor, obtaining second responses of the gas sensor to second dielectric excitation at a second frequency range while the gas sensor is in contact with the an unknown concentration of the gas, and determining, based on the second responses of the gas sensor, and the one or more analytical fit coefficients, the unknown concentration of the gas.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
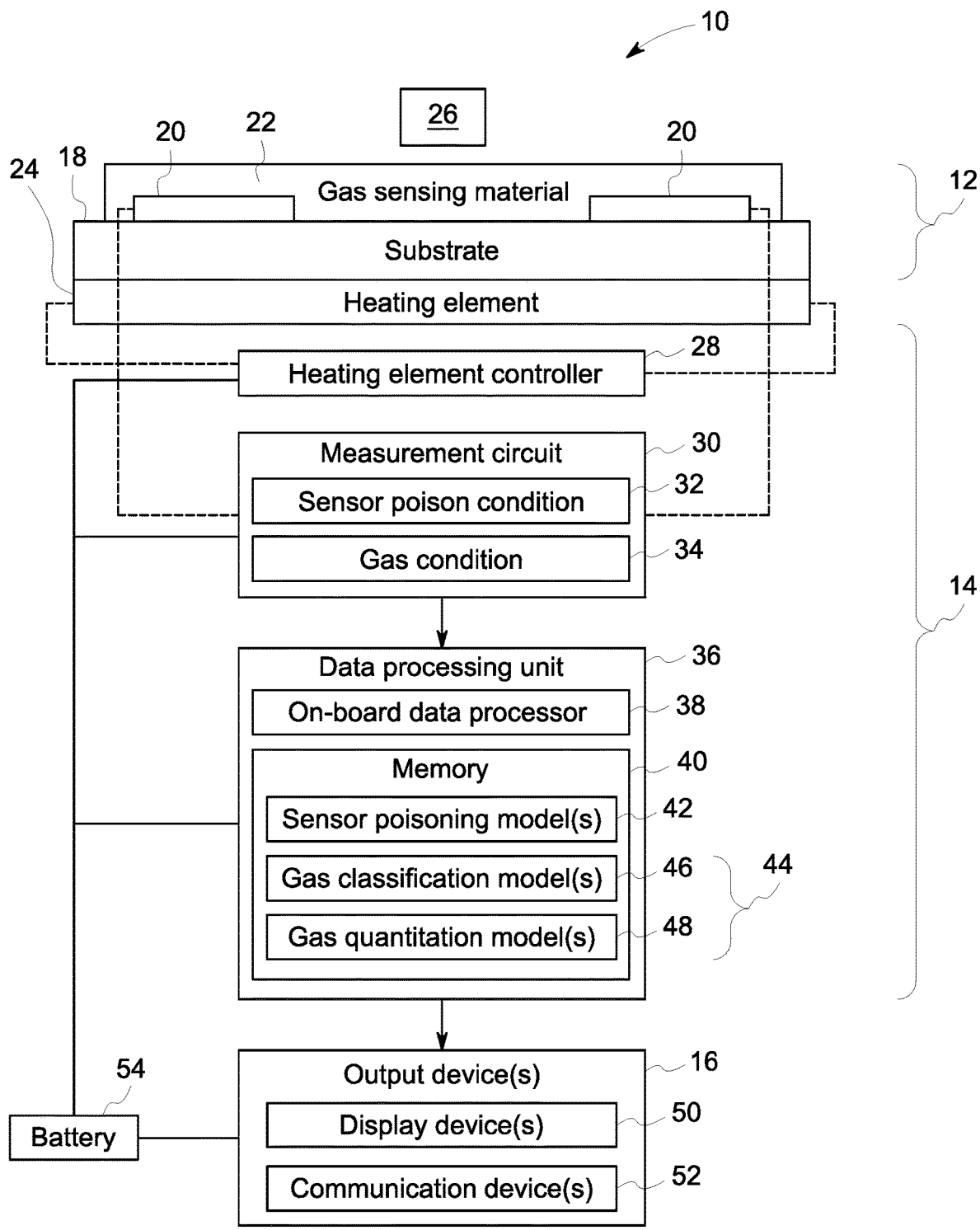
FIG. 1 is a schematic diagram of an embodiment of a gas sensor for gas analysis of fluid samples that can correct for sensor poisoning, in accordance with aspects of the present technique.

Poisoning of metal oxide semiconductor (MOS) sensors with conventional resistance response leads to the loss of the calibration of such sensors. Sensor calibration is a process in which the sensor is exposed to known concentrations of at least one gas, sensor readings are obtained, and a correlation between the known concentrations of the gas and sensor readings is obtained. This correlation may be described or defined as a mathematical transfer function that includes one or more calibration coefficients. Such a transfer function may relate sensor readings to respective gas concentrations employed during the calibration. When a MOS sensor with conventional resistance response is used in practical applications and is poisoned, the sensor calibration may be altered or lost because poisoning changes values of calibration coefficients in mathematical functions that uniquely relate each sensor reading to each gas concentration experienced during the calibration. Thus, in practical applications, resistance readings of poisoned conventional MOS sensors may provide inaccurate values of gas concentrations. Accordingly, poisoned MOS sensors with conventional resistance response may be re-calibrated. A re-calibration includes taking the sensor out of its application environment, bringing the sensor to a dedicated calibration setup, performing a re-calibration of the sensor, and obtaining new values of the calibration coefficients for this sensor. After the re-calibration, the sensor is brought back to its application environment. Accordingly, frequent recalibration of sensors can be resource intensive.

Present embodiments are directed to a system and a method for sensing of at least one gas that determines a sensor poison level of a gas sensor and corrects for the poisoning of the gas sensor. It may be noted that MOS sensing materials are sometimes referred to in the industry as semiconducting metal oxide (SMOX) materials. Exposure to certain vapors or gases (e.g., siloxane vapor) may irreversibly change the response of the MOS sensor to known gases. A MOS sensor with such irreversibly changed response to known gases may be referred to as "poisoning". That is, it is presently recognized that, when a typical MOS sensor has been poisoned, the sensor calibration may be altered or lost because poisoning changes values of calibration coefficients in mathematical functions that uniquely relate each sensor reading to each gas concentration experienced during the calibration. Thus, present embodiments unexpectedly demonstrate MOS-based gas sensors that can determine their own sensor poison level and correct for the sensor poison level to resolve identities of and/or concentrations of at least one gas in a fluid sample. Specifically, the sensor poison level is determined, and then the sensor responses are then adjusted based on the identified sensor poison level. The identities and/or concentrations of gases present in the fluid sample can then be resolved from the adjusted sensor responses as if the sensor was not poisoned.

Contrary to the conventional MOS gas sensor designs with resistance response, present embodiments utilize dielectric excitation at two frequency ranges to determine a poison level of the sensor and account for its effects without re-calibration. Measured sensor response at the first frequency range includes a combination of sensor response to the gas concentrations of the fluid sample and sensor response to the poison level. Measured sensor response at the second frequency range includes sensor response only to the poison level.

The MOS gas sensor is calibrated with dielectric excitation at the first frequency range to known concentrations of at least one gas, sensor readings are obtained, and readings are correlated to the known concentrations of the gas. This correlation may be defined, for example, via a mathematical transfer function that may include one or more calibration coefficients (e.g., analytical fit coefficients). This mathematical function may uniquely relate each sensor reading to each gas concentration employed during the calibration. When a MOS sensor with dielectric excitation at two frequency ranges is used in practical applications and is poisoned, the sensor calibration is self-corrected via the sensor readings at the second frequency range. Thus, in practical applications, readings of poisoned MOS sensors with dielectric excitation at the first frequency range, are self-corrected by the sensor readings at the second frequency range without needing recalibration. Thus, the disclosed gas sensors and gas sensing methods may provide benefits, such as increased lifespan and extended lifetime in environments that may contain sensor-poisoning materials as compared to the conventional MOS gas sensor designs with resistance response.

With the foregoing in mind, FIG. 1 is a schematic diagram of an embodiment of a gas sensor 10 for gas analysis of fluid samples, in accordance with the present technique. In different embodiments, the gas sensor 10 may be a wearable gas sensor, an ingestible gas sensor, a tattooed gas sensor for personal (e.g., patient) monitoring, and so forth. In certain embodiments, the gas sensor 10 may be an industrial environmental sensor, an asset monitoring sensor, an industrial process monitoring gas sensor, a consumer sensor, a transportation sensor, a security sensor, or any combination thereof. In further embodiments, the sensor may be part of a wireless sensor network.

For the embodiment illustrated in FIG. 1, the gas sensor 10 generally includes a gas sensing component 12 (e.g., a gas sensing element), measurement and control circuitry 14, and one or more output devices 16.

The gas sensing component 12 includes a substrate 18 having sensing electrodes disposed thereon. Gas sensing material 22 (e.g., a suitably doped metal oxide semiconductor material (MOS)) may be disposed on the substrate 18 between the sensing electrodes 20. In certain embodiments, there may be more than two sensing electrodes 20, and the sensing electrodes 20 may include a plurality of interdigitated sensing electrodes. In some embodiments, the gas sensing material 22 may include a perovskite oxide with two differently sized cations, or a mixed metal oxide composition, or some combination thereof. Additionally, a resistive heating element 24 is disposed on a surface of the substrate, opposite the gas sensing material 22, and is designed to heat the gas sensing material 22 to a suitable operating temperature (e.g., the temperature to which the gas sensing material 22 is heated for taking measurements) during analysis of at least one gas in a fluid sample 26. The heating element 24 may be disposed on a surface of the substrate 18, opposite the gas sensing material 22, or on the same side of the substrate 18 as the gas sensing material 22.

In some embodiments, the fluid sample may be a particular volume of fluid, in other embodiments, the fluid sample may be a monitored environment of an ambient environment. The fluid sample 26 may include, for example, a gas, a liquid, a gas-liquid mixture, a solid material, particles or particulate matter, or the like, containing one or more gases, including analyte gases and/or interferent gases. In another embodiment, the fluid may be a gas or fuel, such as a hydrocarbon-based fuel. For example, the fluid may be natural gas or hydrogen gas that is supplied to a powered system (e.g., a manned vehicle, an unmanned vehicle, an airplane engine, or a stationary generator set) for consumption. Further, the fluid sample 26 may include gasoline, diesel fuel, jet fuel or kerosene, bio-fuels, petrodiesel-biodiesel fuel blends, natural gas (liquid or compressed), and/or fuel oils. In other embodiments, the fluid sample 26 may be indoor or outdoor ambient air. For example, the air may be from an industrial, residential, military, construction, urban, or any other known site. Further, the ambient air may include relatively small concentrations of benzene, naphthalene, carbon monoxide, ozone, formaldehyde, nitrogen dioxide, sulfur dioxide, ammonia, hydrofluoric acid, hydrochloric acid, phosphine, ethylene oxide, carbon dioxide, hydrogen sulfide, chemical agents such as nerve, blister, blood, and choking agents, hydrocarbons and/or other environmental agents. In other embodiments, the fluid sample 26 may be a disinfecting agent, such as alcohol, aldehyde, chlorine dioxide, hydrogen peroxide, and so forth. In other embodiments, the fluid sample 26 may include ambient air with relatively small concentrations, medium concentrations, and/or large concentrations of combustible gases such as methane, ethane, propane, butane, hydrogen, and/or other gases. In further embodiments, the fluid sample 26 may include at least one gas dissolved in an industrial liquid such as transformer oil, bioprocess media, fermentation media, wastewater, and so forth. The fluid sample 26 may also include at least one gas dissolved in a consumer liquid such as milk, a non-alcoholic beverage, alcoholic beverage, cosmetics, and so forth. In other embodiments, the fluid sample 26 may include at least one gas dissolved in a body liquid such as blood, sweat, tears, saliva, urine, feces, bile, and so forth.

In certain embodiments, the fluid sample 26 may include analyte gases that are toxic industrial materials or toxic industrial chemicals. A non-limiting list of example toxic industrial materials and chemicals includes, but is not limited to, ammonia, arsine, boron trichloride, boron trifluoride, carbon disulfide, chlorine, diborane, ethylene oxide, fluorine, formaldehyde, hydrogen bromide, hydrogen chloride, hydrogen cyanide, hydrogen fluoride, hydrogen sulfide, nitric acid (fuming), phosgene, phosphorus trichloride, sulfur dioxide, sulfuric acid, and tungsten hexafluoride. In certain embodiments, the fluid sample 26 may include analyte gases that are toxic materials of the medium Hazard Index. A non-limiting list of example toxic materials of the medium Hazard Index includes, but is not limited to: acetone cyanohydrin, acrolein, acrylonitrile, allyl alcohol, allylamine, allyl chlorocarbonate, boron tribromide, carbon monoxide, carbonyl sulfide, chloroacetone, chloroacetonitrile, chlorosulfonic acid, diketene, 1,2-dimethylhydrazine, ethylene dibromide, hydrogen selenide, methanesulfonyl chloride, methyl bromide, methyl chloroformate, methyl chlorosilane, methyl hydrazine, methyl isocyanate, methyl mercaptan, nitrogen dioxide, phosphine, phosphorus oxychloride, phosphorus pentafluoride, selenium hexafluoride, silicon tetrafluoride, stibine, sulfur trioxide, sulfuryl chloride, sulfuryl fluoride, tellurium hexafluoride, n-octyl mercaptan, titanium tetrachloride, trichloroacetyl chloride, and trifluoroacetyl chloride.

In certain embodiments, the fluid sample 26 may include analyte gases that are toxic materials of the low Hazard Index. A non-limiting list of example toxic materials of the low Hazard Index includes, but is not limited to: allyl isothiocyanate, arsenic trichloride, bromine, bromine chloride, bromine pentafluoride, bromine trifluoride, carbonyl fluoride, chlorine pentafluoride, chlorine trifluoride, chloroacetaldehyde, chloroacetyl chloride, crotonaldehyde, cyanogen chloride, dim ethyl sulfate, diphenylmethane-4,40-diisocyanate, ethyl chloroformate, ethyl chlorothioformate, ethyl phosphonothioic dichloride, ethyl phosphonic dichloride, ethyleneimine, hexachlorocyclopentadiene, hydrogen iodide, iron pentacarbonyl, isobutyl chloroformate, isopropyl chloroformate, isopropyl isocyanate, n-butyl chloroformate, n-butyl isocyanate, nitric oxide, n-propyl chloroformate, parathion, perchloromethyl mercaptan, sec-butyl chloroformate, tert-butyl isocyanate, tetraethyl lead, tetraethyl pyrophosphate, tetramethyl lead, toluene 2,4-diisocyanate, and toluene 2,6-diisocyanate.

In certain embodiments, the fluid sample 26 may include analyte gases that are indoor pollutants. A non-limiting list of example indoor pollutants includes, but is not limited to: acetaldehyde, formaldehyde, 1,3-butadiene, benzene, chloroform, methylene chloride, 1,4-dichlorobenzene, perchloroethylene, trichloroethylene, naphthalene, and polycyclic aromatic compounds. In certain embodiments, the fluid 26 may include analyte gases that are outdoor pollutants. A non-limiting list of example outdoor pollutants includes, but is not limited to: ozone, nitrogen dioxide, sulfur dioxide, and carbon monoxide.

During operation of the gas sensor 10, the gas sensing material 22 of the gas sensing component 12 is heated as the gas sensing material 22 is exposed to the fluid sample 26, which may include two or more gases, including one or more analyte gases and/or one or more interferent gases. As such, the measurement and control circuitry 14 of the illustrated gas sensor 10 includes a heating element controller 28 that is electrically coupled to the heating element, and that controls the heating element 24 to achieve one or more operating temperatures at which measurements are taken.

For the illustrated embodiment, the sensing electrodes 20 of the gas sensing component 12 are electrically coupled to a measurement circuit 30 of the control circuitry 14 of the gas sensor 10. The measurement circuit 30 is designed to provide at least dielectric excitation (using alternating current) to the gas sensing material 22 at preselected frequencies and to measure dielectric responses of the gas sensing material 22 (e.g., impedance responses) to these excitation frequencies. In certain embodiments, the measurement circuit 30 may additionally be capable of providing direct current (DC) excitations to the gas sensing material 22 and to measure the DC responses (e.g., resistance responses) of the gas sensing material 22 to these excitations. In certain embodiments, the measurement circuit 30 may measure both alternating current (AC) and DC responses of the gas sensing material 22. However, in certain embodiments, the measurement circuit may be designed to only provide dielectric excitation to, and only measure dielectric responses of, the gas sensing material 22. Thus, in certain embodiments, the measurement circuit 30 may be an impedance detector. Typically, MOS gas sensors measure only a DC resistance response. A sensor configured to measure of a single response under a particular excitation condition is referred to as a single-output sensor, the output of which is referred to as a single-output readout.

Specifically, the measurement circuit 30 may be configured to provide first and second dielectric excitation to the gas sensing material 22 at first and second preselected frequencies and to measure first and second dielectric responses of the gas sensing material 22 (e.g., impedance responses) to these first and second excitations, where the response to these first and second excitations may be indicative of a sensor poison condition 32 (e.g., a sensor poison level) of the gas sensing material 22. As used herein, the term impedance is a non-limiting term for any electrical response of the gas sensing component 12 to an alternating electrical current applied to the gas sensing component 12. Such response may be measured as different electrical properties. Non-limiting examples of these different electrical responses of the gas sensing component 12 to alternating electrical current include real part of impedance (Z'), imaginary part of impedance (Z"), admittance, reactance, susceptance, and the like. In the present specification, examples of the responses are given as real part of impedance (Z') and imaginary part of impedance (Z"), however, other electrical responses of the gas sensing component 12 to alternating electrical current are also envisaged.

The response to the first excitation condition may be indicative of a combination of responses to gas concentrations within the fluid sample and to sensor poisoning. The response to the second excitation condition may be indicative of sensor poisoning level. Though the measurement circuit 30 is shown in FIG. 1 as a single circuit, it should be understood that, in some embodiments, and measurement circuit 30 may include multiple components (e.g., sub-components). For example, the measurement circuit 30 may include a first sub-component for determining the sensor poison level of the sensor and a second sub-component for determining identities and/or concentrations of gases within a given fluid sample. The first sub-component for determining the sensor poison level of the sensor may include, for example, a processor to perform data analysis of the sensor responses at two or more frequencies where the data analysis includes performing a set of mathematical operations on the sensor responses at the two or more frequencies. The second sub-component for determining identities and/or concentrations of gases within a fluid sample may include a processor to perform data analysis of the sensor responses at two or more frequencies where the data analysis includes performing the set of mathematical operations on the sensor responses at two or more frequencies. The set of mathematical operations performed by the first sub-component may be different from the set of mathematical operations performed by the second sub-component.

The measurement and control circuitry 14 of the illustrated gas sensor 10 includes a data processing unit 36 (also referred to herein as data processing circuitry) that is communicatively coupled to the measurement circuit 30 to receive the excitation responses measured by the measurement circuit 30. The data processing unit 36 includes an on-board data processor 38 and a memory 40 storing sensor poisoning models 42 and gas analysis models 44, including analyte gas classification models 46, analyte gas quantitation models 48, or any combination thereof. The sensor poisoning models 42 may be mathematical models that model relationships between excitation responses (e.g., dielectric excitation responses) and particular sensor poison levels of the gas sensing materials. As is described in more detail below, once the sensor poison level is known, excitations responses can be corrected (e.g., via a transfer function, a coefficient multiplier, a model, a multivariate statistical model, a machine learning model, and artificial intelligence model, etc.) to resolve identities and/or concentrations of gases in the fluid sample 26. Benefits of performing on-board data processing include fast processing time ranging from 1 second processing time down to 0.1 second processing time, and down to second processing time. The gas analysis models 44 may be mathematical models that model relationships between excitation responses (e.g., dielectric excitation responses) and particular classifications or concentrations of analyte gases in a fluid sample 26. For example, the gas classification models 44 may model relationships between excitation responses of the gas sensing material 22 and particular classifications of analyte gases, while the gas quantitation models 48 may model relationships between excitation responses of the gas sensing material 22 and particular concentrations of analyte gases. In certain embodiments, the sensor poisoning models 42 and the gas analysis models 44 may include one or more coefficients that are experimentally determined and stored in the memory 40.

As discussed below, the on-board data processor 38 receives the excitation responses measured by the measurement circuit 30, selects a first set of particular excitation responses (e.g., dielectric excitation responses) for analysis, and provides these excitation responses as inputs to one or more of the sensor poisoning models 42, wherein the sensor poisoning models 42 return outputs that identify a sensor poison level of the gas sensing material 22. Sensor poisoning models 42 may be based on multivariate statistical models, machine learning models, and artificial intelligence models. The on-board data processor 38 then selects a second set of particular excitation responses (e.g., dielectric excitation responses) for analysis, and provides these excitation responses, along with the determined sensor poison level, as inputs to one or more of the stored gas analysis models 44, wherein the gas analysis models 44 return outputs that resolve two or more analyte gases in the fluid sample 26. As used herein, "resolving" two or more analyte gases in a fluid sample, or "providing resolution" between two or more analyte gases in a fluid sample, refers determining a respective classification for each of the analyte gases in the fluid sample, determining a respective concentration of the analyte gases in the fluid sample, or determining both respective classifications and respective concentrations of analyte gases in the fluid sample. As used herein, "classifying" or "determining a classification of" an analyte gas refers to determining an exact chemical identity (e.g., ethanol, acetone, methanol) of the analyte gas or determining a chemical class (e.g., a hydrocarbon, alcohol, phenol, ether, aldehyde, ketone, carboxylic acid, ester, and so forth) to which each analyte gas belongs. As used herein, an "unselected" response refers an excitation response that is measured by the measurement circuit 30 and is not used by the on-board data processor 38 during analysis to resolve the analyte gases in the fluid sample 26.

In certain embodiments, the memory 40 may be integrated into the on-board data processor 38. In certain embodiments, the on-board data processor 38 may be a multicore processor. For example, in some embodiments, the on-board data processor 38 may be a multicore processor on a single integrated circuit with two or more separate processing units (or cores), each of which reads and executes program instructions. In certain embodiments, the multicore processor may only include a single central processing unit (CPU) and multiple additional cores. For embodiments in which the on-board data processor 38 is a multicore processor, different sensor poisoning models 42, gas analysis models 44, and/or different signal processing algorithms may be independently executed by different cores to reduce the power consumption of the data processing unit 36 and/or the gas sensor 10.

For the illustrated embodiment, the gas sensor 10 includes one or more output devices 16. In certain embodiments, the output devices 16 may include one or more display devices 50 that are configured to present information regarding analysis of at least one gas, such as the poison level of the sensor, as well as the classification and/or concentration of two or more analyte gases in the fluid sample 26. In some embodiments, other output devices 16 (e.g., speakers, light emitting diodes (LEDs), haptic feedback devices) may be included. Accordingly, the output devices 16 may be configured to generate alarms (e.g., visual alarms, audible alarms, haptic alarms, etc.) when certain conditions are detected. In certain embodiments, the output devices 16 may include one or more communication devices 52 (e.g., wired communication interfaces, wireless communication interfaces) that enable the gas sensor 10 to communicate with other computing systems, such as a desktop computer, a mobile computing device (e.g., a laptop, smart phone), a remote server (e.g., an Internet server, a cloud server), or other sensors (e.g., gas sensors, temperature sensors, vibration sensors, health monitors) of a multi-sensor monitoring system. For example, in certain embodiments, information determined by the on-board data processor 38 regarding the sensor poison level of the gas sensing materials 22, and/or the resolution of two or more analyte gases in the fluid sample 26, may be provided to an external computing system that serves as a controller of a mesh of sensors that includes the gas sensor 10. In some embodiments, the gas sensor 10 may additionally or alternatively use the communication devices 52 to provide excitation response measurements to an external computing system, such that the external computing system can use these measurements to calculate one or more coefficient values for one or more of the gas analysis models and return these coefficient values to the gas sensor 10 for storage in the memory 40.

Additionally, the illustrated gas sensor 10 includes a battery 54 that is electrically coupled to provide power to various components of the gas sensor 10, including the control circuitry 14 and the output devices 16. It may be appreciated that the battery 54 may have a suitable capacity to power all of the components of the gas sensor 10. For example, this may include: heating the gas sensing material 22, providing dielectric excitation to the gas sensing material 22, measuring the dielectric excitation responses of the gas sensing material 22, analyzing the measured dielectric excitation responses to resolve two or more gases in a fluid sample, and presenting results of the analysis via a suitable output devices 16. In certain embodiments, the battery 54 may have a capacity that is sufficient to operate the gas sensor 10 for at least 10 hours. For example, the battery 54 may have a capacity ranging from 1 milliamp-hour (mAh) to 500 mAh, 1 mAh to 200 mAh, or 1 mAh to 100 mAh, or some other range. In certain embodiments, such as embodiments in which the gas sensor 10 is designed to be particularly thin (e.g., for ingestible or tattooed embodiments of the gas sensor 10), the battery 54 may have a thickness less than about 5 millimeters (mm). In some embodiments, all of the components of the gas sensor 10 may be coupled to or at least partially disposed within a suitable packaging or housing for a particular gas sensing application. For example, for personal monitoring applications, the packaging of the gas sensor 10 may be made of a biocompatible polymer that can be externally worn, subcutaneously injected, or ingested to perform personal or patient analysis of at least one gas.

In some embodiments, the gas sensor 10 system may be a wearable device that may be worn or otherwise moved from place to place by an operator. In such embodiments, the gas sensor 10 may be positioned in or be an integrated part of a helmet, hat, glove, or other articled of clothing/equipment. For example, the gas sensor 10 may be disposed within a wearable or non-wearable transferable object, such as a frame of military or industrial eyeglasses, a wearable pulse oximeter, a safety vest or harness, an article of clothing, a mobile device (e.g., a cellular phone, a tablet, or the like), or the like. The wearable device may be integrated into a piece of fabric of clothing, can be positioned on clothing, such as on a pocket, in an arm band, worn on a wrist, or other extremity, and the like. The wearable gas sensor 10 can be fabricated using manufacturing technologies based on complementary metal-oxide-semiconductor electronics, flexible electronics, flexible hybrid electronics, and other approaches to provide conformal and flexible designs, implementations, and use. Optionally, the system may be a stationary device, may be independently mobile (e.g., detachable from an operator and capable of moving independent of the operator), may be airborne, and so forth.

In one or more embodiments, the gas sensor 10 may be a wearable sensor system, may be held within a wearable and/or non-wearable transferrable object (e.g., a frame of military or industrial eyeglasses), or the like. The wearable gas sensor 10 may be worn by a subject, such as a human or animal or a robot, may be removably coupled or integrated with an article worn by a subject (e.g., a shirt, pants, safety vest, safety personal protection clothing, eyeglasses, hat, helmet, hearing device, etc.), or may be any alternative device that may be transferrable such that gas sensor 10 can be moved between different positions, may be stationary or substantially stationary, or the like.

The gas sensor 10 may be in contact with the fluid sample 26 in the form of a fluid vessel that may have controlled volume or an open area, such as an indoor facility (e.g., a room, a hall, a house, a school, a hospital, a confined space, or the like), or in an outdoor facility (e.g., a stadium, a gas-production site, fueling stations, gasoline fueling stations, hydrogen fueling stations, compressed natural gas fueling stations, liquefied natural gas fueling stations, gas distribution site, fuel distribution site, a seashore, a forest, a city, urban environment, marine environment, and so forth). In some embodiments, the gas sensor 10 may provide continuous monitoring of the fluid sample 26 within the reservoir or flow path. In one or more embodiments, the gas sensor 10 may be an impedance gas sensor, an electromagnetic sensor, an electronic sensor, a hybrid sensor, or another type of sensor. Optionally, the multivariable gas sensor 10 may be a sensor array. In some embodiments, the sensor 10 may be implemented in applications such as outdoor/indoor air quality, homeland security, industrial safety, environmental monitoring, process control, disease diagnostics, etc. In other embodiments, the sensor 10 may be used to detect toxic household and/or industrial chemical, environmental emissions, and/or industrial emissions. In further embodiments, the sensor 10 may be used for detection of volatiles in exhaled breath, inside a gastrointestinal tract, intestinal gas production, volatolomics, and from other emission sources from humans.

The wearable gas sensor 10 may be worn, or otherwise carried, by different subjects or individuals, such as, but not limited to, soldiers, medical professionals, athletes, system operators, students otherwise active or inactive individuals, or the like. Optionally, the wearable gas sensor 10 may be coupled with, integrated with, disposed on, or the like, an asset, such as a moving system such as a drone, a stationary system, or the like. The wearable gas sensor 10 may be positioned on items worn by the subject, such as helmets, pockets (e.g., of shirts, pants, bags, or the like), gloves, arm bands, ear pieces, or the like, or may be attached or otherwise coupled directly to the subject or asset, such as on the wrist, around an ankle, or the like.

The gas sensor 10 may represent one or more different versions of multi-gas sensing systems described herein. In one or more embodiments, the measurement circuit may include a resistor-capacitor (RC) electrical circuit that includes one or more resistor (R) and capacitor (C) components that may be electronically changed by a control circuitry 14 by the presence of one or more analyte gases of interest. In one or more embodiments, the measurement circuit 30 may perform dielectric excitation and impedance measurements at one or more different frequencies or at one or more different RC configurations of the measurement circuit 30. For example, the measurement circuit 30 of the gas sensor 10 may measure impedance responses of the gas sensing material 22 at different frequencies, at different resistances of the RC electrical circuit of the measurement circuit 30, at different capacitances of the RC electrical circuit of the measurement circuit 30, or any combination thereof. The measurement circuit 30 provides excitation and measurement of the response of the sensing element 12 to gases. The sensing element is predictably affected by the measured gas concentrations, whereas the measurement circuit 30 may not be affected by the measured gas concentrations.

A gas sensing element 12 that has two or more responses or outputs may be referred to as a multivariable gas sensing element 12. Multivariate data processing principles may be applied to analyze outputs from a multivariable gas sensing element 12 to quantify diversity of responses of a multivariable gas sensing element to different gases. Multivariate transfer functions can be developed and implemented to quantify different gases in new measurement data collected from the multivariable gas sensing element.

Multivariate data processing principles may include, for example, techniques for classification/cluster analysis and quantitation of gases. Classification/cluster analysis can be performed to determine the type of the analyte gas in a fluid sample. Quantitation can be performed to determine the concentration of the analyte gas in the fluid sample. Examples of classification/cluster analysis algorithms include, for example, Principal Component Analysis (PCA), Hierarchical Cluster Analysis (HCA), Independent Component Analysis (ICA), Linear Discriminant Analysis (LDA), and Support Vector Machines (SVM) algorithm. Techniques for performing analyte quantitation to determine the concentration of a particular analyte gas may include, for example, Principal Component Regression (PCR), Independent Component Regression (ICR), Nonlinear Regression Analysis (NRA), Discriminate Function Analysis (DFA), or Artificial Neural Network Analysis (ANN). In some embodiments, application of a classification algorithm may be followed by application of a quantitation algorithm.

Figure 2:
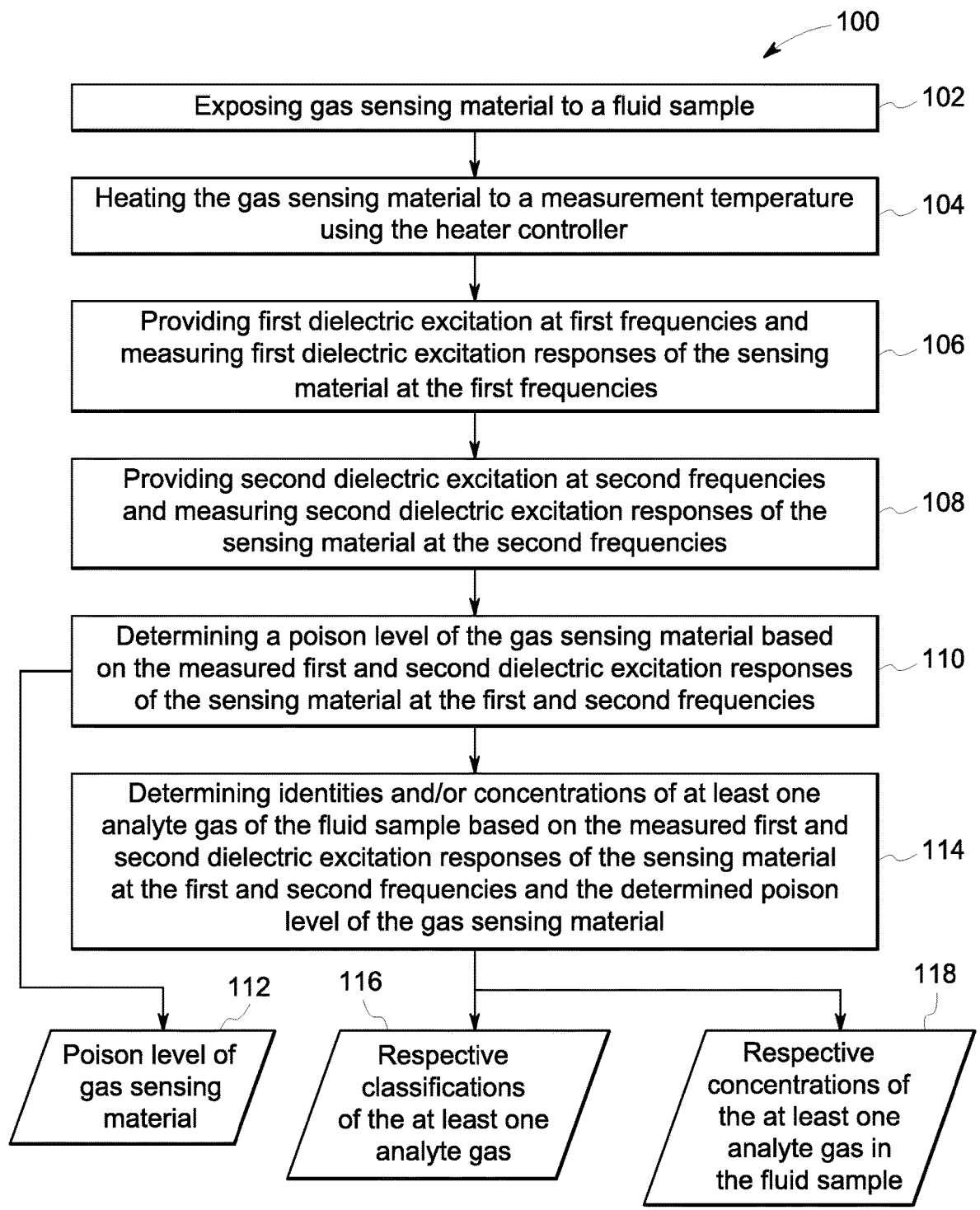
FIG. 2 is a flow diagram illustrating an embodiment of a process whereby the gas sensor performs analysis of one or more gases while correcting for sensor poisoning, in accordance with aspects of the present technique.

FIG. 2 is a flow diagram illustrating an embodiment of a process 100 whereby the gas sensor 10 performs analysis of at least one gas in a fluid sample 26. The process 100 begins with exposing (block 102) the gas sensing material 22 of the gas sensing component 12 to a fluid sample 26 having at least one gas, including at least one analyte gas and/or one or more interferent gases.

At block 104, the gas sensing material 22 is heated to an operating temperature using the heating element controller 28. In some embodiments, the operating temperature may be a single, constant, temperature. In other embodiments, the gas sensing material 22 may be heated to multiple operating temperatures. In such embodiments, the heating element controller 28 may be configured to heat the gas sensing material 22 such that the gas sensing material 22 reaches steady state at multiple operating temperatures, or the heating element controller 28 may be configured to heat the gas sensing material 22 such that the gas sensing material 22 reaches multiple operating temperatures without reaching steady state, at one or more of the operating temperatures. In embodiments in which multiple operating temperatures are used, the cycle periodicity may be one cycle in 10 minutes, one cycle in 1 minute, one cycle in 10 seconds, one cycle in 1 second, one cycle in 0.1 seconds, one cycle in 0.01 seconds, or any other period of time.

At block 106, the measurement circuit 30 provides first dielectric excitation using preselected frequencies to the gas sensing material 22 operating at the operating temperature(s), and then measures first dielectric excitation responses (e.g., real and/or imaginary impedance responses) of the gas sensing material 22. As discussed in more detail below, the first dielectric excitation responses may be indicative of identities and/or concentrations of analyte gases within the fluid sample and a sensor poison level of the gas sensor 10. In certain embodiments, the measurement circuit 30 may additionally apply DC excitation to the gas sensing material 22 and measure DC excitation responses (e.g., resistance responses) of the gas sensing material 22 at the operating temperature(s). However, in some embodiments, the measurement circuit 30 may only measure dielectric excitation responses of the gas sensing material 22 as it contacts the fluid sample 26 at the operating temperature(s).

At block 108, the measurement circuit 30 provides second dielectric excitation using preselected frequencies to the gas sensing material 22 operating at the operating temperature(s), and then measuring dielectric excitation responses (e.g., real and/or imaginary impedance responses) of the gas sensing material 22. The preselected frequencies for the second dielectric excitation may be selected based upon their placement on an impedance spectrum of the gas sensing material. For example, one or more of the preselected frequencies for the second dielectric excitation may be selected based upon its placement on a shoulder of a dielectric relaxation region on an impedance spectrum of the gas sensing material. In some embodiments, the preselected frequencies for the second dielectric excitation may be higher frequencies than each of the preselected frequencies for the first dielectric excitation. Further, in some embodiments, the preselected frequencies for the second dielectric excitation may be selected based upon the determined or predicted sensor poison level of the gas sensing component 12. As discussed in more detail below, the second dielectric excitation responses may be indicative of the sensor poison level of the gas sensor 10. In certain embodiments, the measurement circuit 30 may additionally apply DC excitation to the gas sensing material 22 and measure DC excitation responses (e.g., resistance responses) of the gas sensing material 22 at the operating temperature(s). However, in some embodiments, the measurement circuit 30 may only measure dielectric excitation responses of the gas sensing material 22 as it contacts the fluid sample 26 at the operating temperature(s).

Traditionally, MOS gas sensors 10 measure a DC resistance response of a MOS-based sensing element 12 and relate the measured DC resistance response to a concentration of a gas using a power-law relation between the measured resistance and gas concentration. Such DC resistance responses from a MOS gas sensor 10 may be provided as a signal output (e.g., to a user) in a form of an analog signal. Depending on the design of an analog circuit, an analog signal from a MOS gas sensor 10 may represent linear resistance, logarithmic resistance, or conductivity. Alternatively DC resistance responses from a traditional MOS-based gas sensor 10 may be provided as a signal output in a form of a digitized DC resistance response signal. Dependent upon the design of an analog/digital circuit, the digital signal from a MOS gas sensor 10 may be correlated with linear resistance, logarithmic resistance, or conductivity. A digital signal from a MOS gas sensor 10 that is correlated with its DC resistance response can be provided (e.g., to the user) by any of digital communication protocols, for example an I2C (Inter-Integrated Circuit), alternatively known as IIC, and any other communication protocols.

At block 110, the on-board data processor 38 of the gas sensor 10 performs on-board data analysis of the first and second measured dielectric excitation responses based on at least one of the sensor poisoning models 42 to determine and output a sensor poison level 112 of the gas sensor 10. As discussed previously with regard to FIG. 1, the poison level 112 may be determined by applying one or more sensor poisoning models 42 (e.g., mathematical models) that model relationships between excitation responses and particular sensor poison levels of the gas sensing materials 22. In some embodiments, this may involve evaluating the excitation responses at multiple frequencies to identify one or more frequencies at which the different sensor poison levels are discernable. In some embodiments, the sensor poison level 112 may be a value that indicates the sensor poison level of the gas sensing materials 22, which may be applied to the excitation responses to generate corrected responses such that identities and/or concentrations of gases in the fluid sample 26 can be determined. In other examples, the sensor poison level 112 may be provided to a transfer function, a lookup table, a model, a coefficient multiplier, etc. may be applied to measured response data to generate corrected excitation responses, from which identities and/or concentrations of gases in the fluid sample 26 can be determined. In some embodiments, the transfer function, the lookup table, and/or the model, etc. may be selected based on the determined sensor poison level of the sensor. In other embodiments, the transfer function may be generated and/or updated based upon the determined sensor poison level 112. In some embodiments, the transfer function may be generated based on an imaginary part of impedance spectra, a real part of impedance spectra, or both. The real and/or imaginary parts of impedance spectra may be generated based on the first dielectric excitation at the first set of frequencies, the second dielectric excitation at the second set of frequencies, or both. Further, the transfer function may be updated when new data is collected, on a periodic basis, upon some triggering event taking place, and so forth. Accordingly, recalibration of the transfer function may occur on a periodic basis, as opposed to being part of a standard measurement cycle. Sensor analysis is performed on a cyclical basis (such as monthly, quarterly, annually, etc.) and changes in measurement performance may be corrected based on a recalibration.

At block 114, the on-board data processor 38 of the gas sensor 10 performs on-board data analysis of the first and second measured dielectric excitation responses based on the sensor poison level 112 of the gas sensor 10, as well as at least one of the stored gas analysis models 44 to provide a real-time resolution of the analyte gases in the fluid sample. That is, at block 114, the system may output respective classifications of two or more analyte gases within the fluid sample 116 and/or respective concentrations of two or more analyte gases within the fluid sample 118. For certain embodiments in which DC excitation responses are also measured by the measurement circuit 30, the on-board data processor 38 may also provide these DC excitation responses as inputs to at least one of the sensor poisoning models 42, and/or the stored gas analysis models 44 when resolving the analyte gases in the fluid sample. In this context, "real-time" refers to the on-board data processor 38 of the gas sensor 10 being able to locally, rapidly resolve analyte gases in the fluid sample without requiring the measured excitation responses be provided to an external computing system for processing. For example, in some embodiments, the data processing unit 36 may be configured to identify one or more frequencies of the first and/or second frequencies at which the response of the gas sensing material to the first and/or second dielectric excitation is linear or substantially linear (e.g., the coefficient of determination value of the linear fit is greater than 0.9, 0.95, 0.96, 0.97, 0.98, 0.99, etc.). The data processing unit 36 may then apply a transfer function (e.g., based on the determined poison level 112 of the gas sensing material) to the data collected from the response of the gas sensing material to the first dielectric excitation at the one or more frequencies of the first set of frequencies (at block 106), and/or the second dielectric excitation at the one or more frequencies of the second set of frequencies (at block 108), to generate corrected response data that corrects for the sensor poison level. However, in other embodiments, a multiplier coefficient, a lookup table, a model, etc. may be applied to the data collected from the response of the gas sensing material to the first and/or second dielectric excitation to correct for and/or account for the poison level of the sensor.

The analyte gases may include a wide range of materials and/or chemicals of various hazard indexes. Materials having a "high" hazard index may include, for example, Ammonia, Arsine, Boron trichloride, Boron trifluoride, Carbon disulfide, Chlorine, Diborane, Ethylene oxide, Fluorine, Formaldehyde, Hydrogen bromide, Hydrogen chloride, Hydrogen cyanide, Hydrogen fluoride, Hydrogen sulfide, Nitric acid, fuming, Phosgene, Phosphorus trichloride, Sulfur dioxide, Sulfuric acid, and Tungsten hexafluoride.

Materials having a "medium" hazard index may include, for example, Acetone cyanohydrin, Acrolein, Acrylonitrile, Allyl alcohol, Allylamine, Allyl chlorocarbonate, Boron tribromide, Carbon monoxide, Carbonyl sulfide, Chloroacetone, Chloroacetonitrile, Chlorosulfonic acid, Diketene, 1,2-Dimethylhydrazine, Ethylene dibromide, Hydrogen selenide, Methanesulfonyl chloride, Methyl bromide, Methyl chloroformate, Methyl chlorosilane, Methyl hydrazine, Methyl isocyanate, Methyl mercaptan, Nitrogen dioxide, Phosphine, Phosphorus oxychloride, Phosphorus pentafluoride, Selenium hexafluoride, Silicon tetrafluoride, Stibine, Sulfur trioxide, Sulfuryl chloride, Sulfuryl fluoride, Tellurium hexafluoride, n-Octyl mercaptan, Titanium tetrachloride, Trichloroacetyl chloride, and Trifluoroacetyl chloride.

Materials having a "low" hazard index may include, for example, Allyl isothiocyanate, Arsenic trichloride, Bromine, Bromine chloride, Bromine pentafluoride, Bromine trifluoride, Carbonyl fluoride, Chlorine pentafluoride, Chlorine trifluoride, Chloroacetaldehyde, Chloroacetyl chloride, Crotonaldehyde, Cyanogen chloride, Dimethyl sulfate, Diphenylmethane-4,40-diisocyanate, Ethyl chloroformate, Ethyl chlorothioformate, Ethyl phosphonothioic dichloride, Ethyl phosphonic dichloride, Ethyleneimine, Hexachlorocyclopentadiene, Hydrogen iodide, Iron pentacarbonyl, Isobutyl chloroformate, Isopropyl chloroformate, Isopropyl isocyanate, n-Butyl chloroformate, n-Butyl isocyanate, Nitric oxide, n-Propyl chloroformate, Parathion, Perchloromethyl mercaptan, sec-Butyl chloroformate, tert-Butyl isocyanate, Tetraethyl lead, Tetraethyl pyrophosphate, Tetramethyl lead, Toluene 2,4-diisocyanate, and Toluene 2,6-diisocyanate. Analyte gases may also include a range of indoor environmental agents, such as Acetaldehyde, Formaldehyde, 1,3-Butadiene, Benzene, Chloroform, Methylene chloride, 1,4-Dichlorobenzene, Perchloroethylene, Trichloroethylene, Naphthalene, Polycyclic aromatic compounds, as well as outdoor environmental agents, such as Ozone, Nitrogen dioxide, Sulfur dioxide, Carbon monoxide. Further, the analyte gases may include industrial agents, such as combustibles, confined space hazards, and so forth.

For the embodiment of the process 100 illustrated in FIG. 2, after resolving the analyte gases in the fluid sample 26, the gas sensor 10 may use one or more output devices 16 to output the respective classifications 80 of the analyte gases in the fluid sample, the respective concentrations 82 of the analyte gases in the fluid sample, the sensor poison level of the gas sensor 10, or some combination thereof. For example, one or more output devices 16 of the gas sensor 10 may present or display the respective classifications 80, the respective concentrations 82 of the analyte gases in the fluid sample 26, the sensor poison level of the gas sensor 10, or some combination thereof. In certain embodiments, the gas sensor 10 may provide the respective classifications 80, the respective concentrations 82 of the analyte gases, the sensor poison level of the gas sensor 10, or some combination thereof, to an external computing system via one or more suitable communication devices (e.g., a wireless communication interface) of the gas sensor 10.

Figure 3:
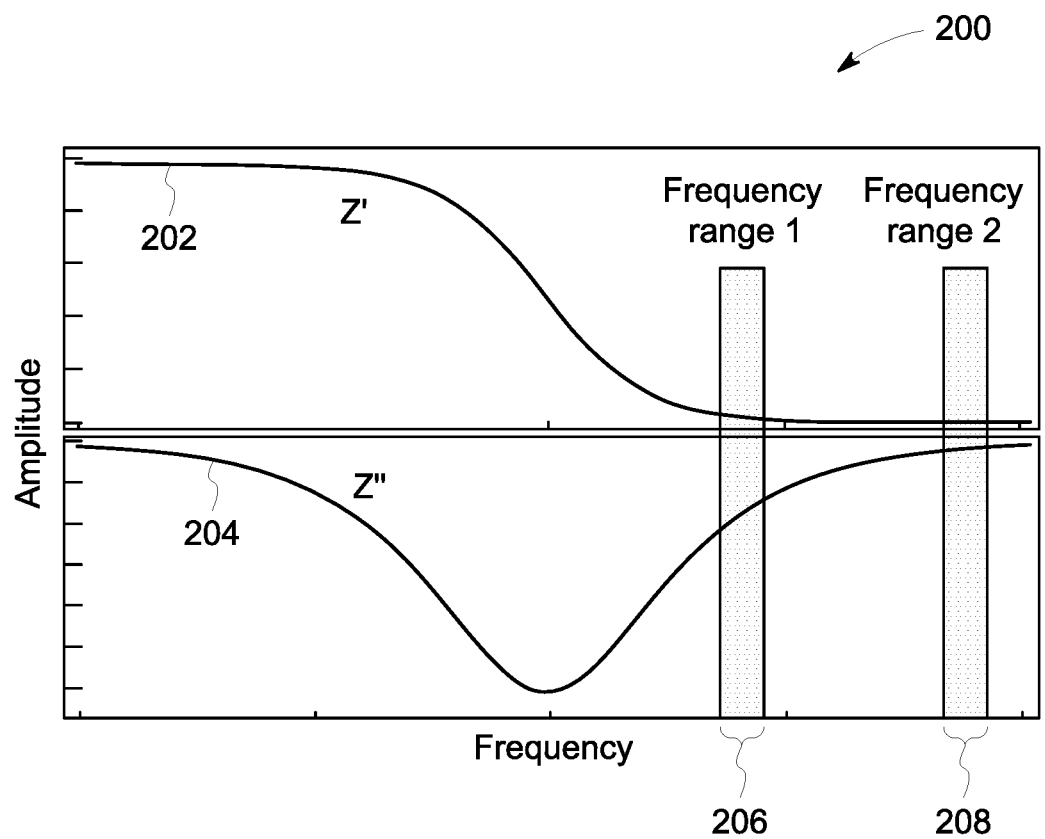
FIG. 3 is a graph of an example impedance spectrum showing a real part (Z') and an imaginary part (Z") of the impedance spectrum of a gas sensing material of the gas sensor of FIG. 1 with preselected frequencies for dielectric excitation, in accordance with aspects of the present technique.

FIG. 3 is a graph illustrating an example impedance spectrum 200. In impedance spectroscopy, measurements of the real part (Z') and the imaginary part (Z") of the impedance may be performed over a range of frequencies to determine the shape of the impedance spectrum 200 of the gas sensor 10. As illustrated, the impedance spectrum includes two curves, each representing part of the impedance response of the gas sensor 10 over a range of frequencies to determine the shape of the impedance spectrum. In particular, a first curve 202 represents the real part (Z') of the impedance of gas sensor 10, while a second curve 204 represents the imaginary part (Z") of the impedance of the gas sensor 10 as measured over the range of frequencies. Unlike broad-band impedance spectroscopy measurements, the dielectric excitation measurements are performed over specific frequency ranges by following the front (high- or low-frequency) shoulder of the dielectric relaxation region obtained from impedance measurements of (n- or p-type, respectively) MOS materials when they are exposed to various gas concentrations.

For present embodiments, the measurement circuit includes an impedance detector that measures the dielectric excitation response of the gas sensor 10 at two or more frequency ranges 206, 208 (which may or may not be disposed in the "dielectric relaxation region" of the gas sensor 10). For example, in certain embodiments, each dielectric excitation response measured by the measurement circuit and may include a combination (e.g., a sum, a difference, any other mathematical representation) of a value from the first curve 202 (e.g., a real impedance value) and a value from the second curve 204 (e.g., an imaginary impedance value), both selected from the frequency ranges 206, 208.

In other embodiments, each dielectric excitation response measured by the measurement circuit may include a combination (e.g., a sum, a difference, any other mathematical representation) of a value from the first curve 202 (e.g., a real impedance value Z') and a value from the second curve 204 (e.g., an imaginary impedance value Z"), both selected from the frequency ranges 206, 208, or other frequency ranges.

Selection of the frequency ranges 206, 208 may depend on type of the gas sensing element 12 of the gas sensor 10. For example, related to the gas sensing element 12, the selection of the frequency ranges 206, 208 may depend on the type of the MOS sensing material, for example n-type or p-type or a combination of n- and p-type MOS sensing material and type of gases for measurements such of reducing gases or oxidizing gases. As a result, either the high-frequency shoulder region or the low-frequency shoulder region may be selected for measurements. For example, response at the frequency ranges 206, 208 may include data indicative of sensor response to gases in the fluid sample. The identities and/or concentrations of gases in the fluid sample may then be determined based on the sensor response at the first and second frequency ranges 206, 208.

Use of the disclosed techniques may unexpectedly improve various characteristics of the gas sensor, such as increased lifespan in environments that may contain sensor-poisoning materials. Further, by utilizing the presently disclosed techniques, a sensor may continue to be used and may continue to output accurate results after poisoning, thus extending the usable life of such gas sensors in environments where sensor poisoning gases may be present. In certain embodiments, extending the usable life of gas sensors may also extend a maintenance cycle of the gas sensor, resulting in less frequent re-calibration of the gas sensor. In certain embodiments, operation of the gas sensor after poisoning may include the implementation of at least one transfer function that may correct for the poison level of the gas sensor in real-time during operation of the sensor in a normal operating mode of the gas sensor without cycling power to the gas sensor, without removal of the sensor from the measurement system and/or prescribed location where the sensor is being operated, without transporting the gas sensor to a different location for calibration, and without the use of a calibration gas To further demonstrate the superior performance of the disclosed techniques, experiments were performed to account for sensor poisoning of the gas sensing materials 22 when the gas sensor is exposed to siloxane vapor. For these experiments, all measurements were performed using a metal-salt-doped tin oxide ($SnO_2$) as the gas sensing material 22. The measurements were performed by the using measurement circuit 30 such as an impedance detector as dielectric excitation responses (e.g., real and imaginary impedance measurements) selected from the high-frequency shoulder region of corresponding impedance spectra 200 after dielectric excitation. The gas sensor 10 was exposed to ten different concentration levels of methanol vapor: 6.25 parts-per-million (ppm), 12.50 ppm, 18.75 ppm, 25.00 ppm, 31.25 ppm, 37.50 ppm, 43.75 ppm, 50.00 ppm, 56.25 ppm, and 62.50 ppm. A first test was conducted before the gas sensing material 22 was exposed to siloxane vapor. The gas sensing material 22 was exposed to 4500 ppm siloxane vapor for 20 minutes and then second and third tests were conducted. The gas sensing material 22 was exposed to the 4500 ppm siloxane vapor for an additional 80 minutes and then fourth and fifth tests were conducted. As such, for the experiments illustrated by FIGS. 4-7, the gas sensor 10 was: (A) heated to a first operating temperature, (B) exposed to each of the ten concentrations of methanol vapor, (C) exposed to 4500 ppm siloxane vapor for 20 minutes, (D) exposed to each of the ten concentrations of methanol vapor a second time, (E) exposed to each of the ten concentrations of methanol vapor a third time, (F) exposed to 4500 ppm siloxane vapor for an additional 80 minutes, (G) exposed to each of the ten concentrations of methanol vapor a fourth time, and (H) exposed to each of the ten concentrations of methanol vapor a fifth time.

Figure 4A:
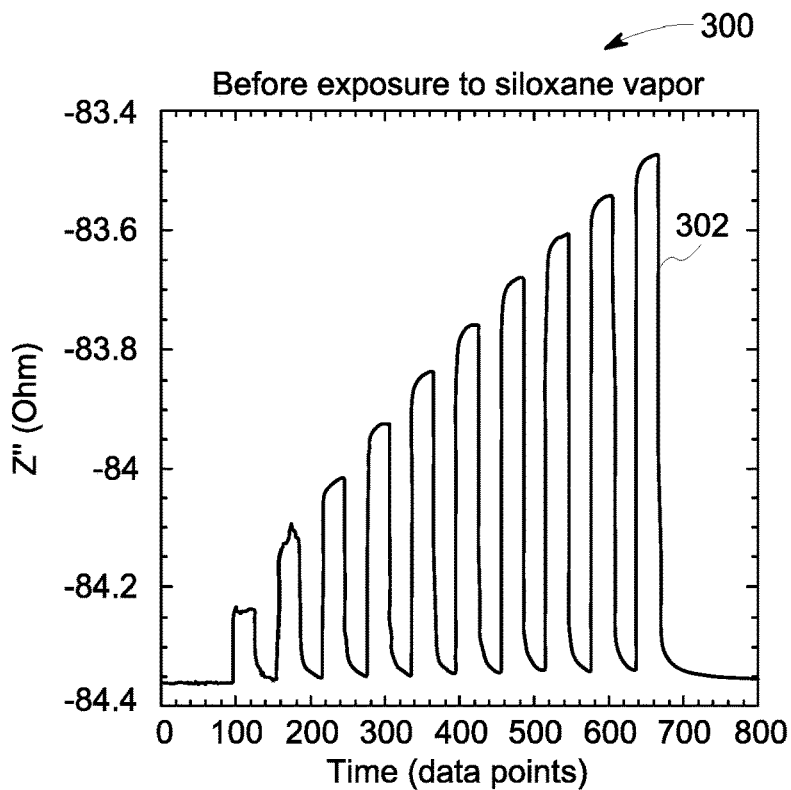
FIG. 4A is a graph depicting an example of an imaginary part of an impedance response pattern of the gas sensor to ten concentrations of methanol vapor at 0.7 MHz, prior to exposure to siloxane vapor, in accordance with aspects of the present technique.
Figure 4B:
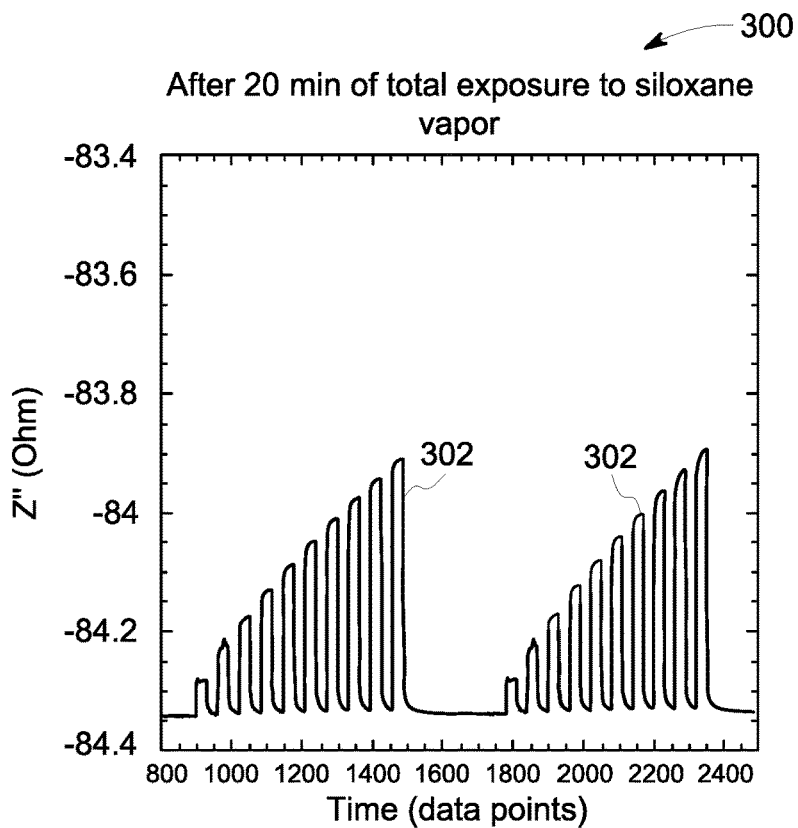
FIG. 4B is a graph depicting an example of an imaginary part of an impedance response pattern of the gas sensor to the ten concentrations of methanol vapor with two replicates at 0.7 MHz, after 20 minutes of exposure to the siloxane vapor, in accordance with aspects of the present technique.
Figure 4C:
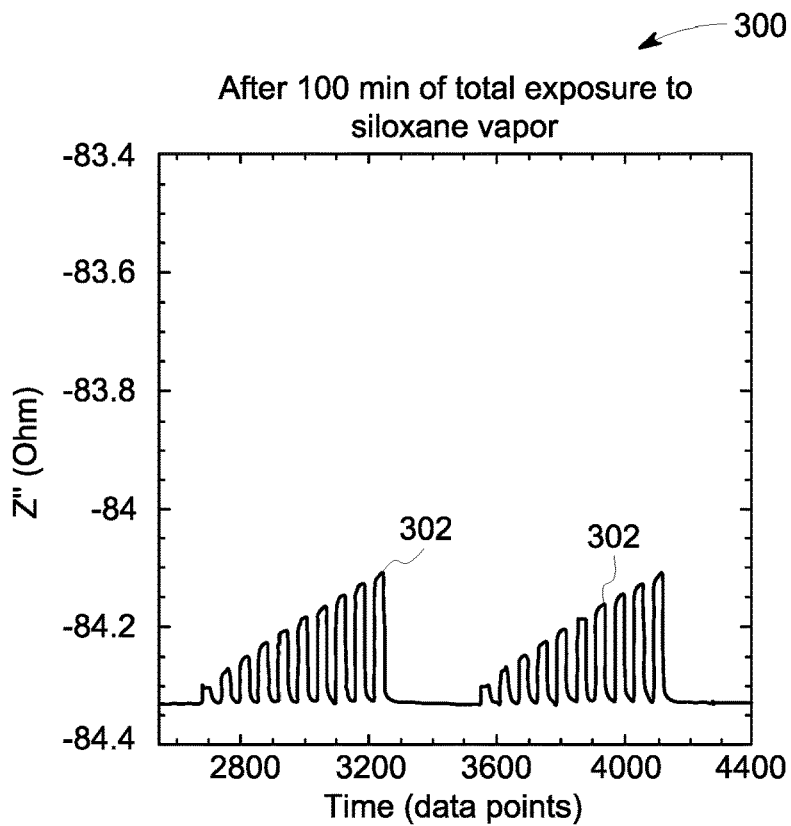
FIG. 4C is a graph depicting an example of an imaginary part of an impedance response pattern of the gas sensor to the ten concentrations of methanol vapor with two replicates at 0.7 MHz, after 100 minutes of exposure to the siloxane vapor, in accordance with aspects of the present technique.

FIGS. 4A-4F are graphs 300 depicting examples of response patterns of the gas sensing material 22 to the ten concentrations of methanol vapor, at two different frequencies (0.7 MHz and 12.6 MHz) after 0 minutes, 20 minutes, and 100 minutes of exposure time to 4500 ppm siloxane vapor. For each graph 300, the horizontal axis represents time while the vertical axis represents impedance. Specifically, the responses shown in FIGS. 4A-4C represent the imaginary part 302 (second curve 204 in FIG. 3) of the measured impedance at the high frequency shoulder region 206 of the gas sensing material 22 at 0.7 MHz. As shown, at 0.7 MHz, the response of the gas sensing material 22 is substantially linear before sensor poisoning, after 20 minutes of exposure to the siloxane vapor, and after 100 minutes of exposure to siloxane vapor, however, the magnitude of the responses decreased as the time of exposure of the gas sensing material 22 to the siloxane vapor increased. Accordingly, these results indicate that a transfer function can be generated based on the poison level of the sensor to correct data collected from the poisoned sensor. Accordingly, the corrected data output by the transfer function should appear as though it comes from an un-poisoned sensor.

Figure 4D:
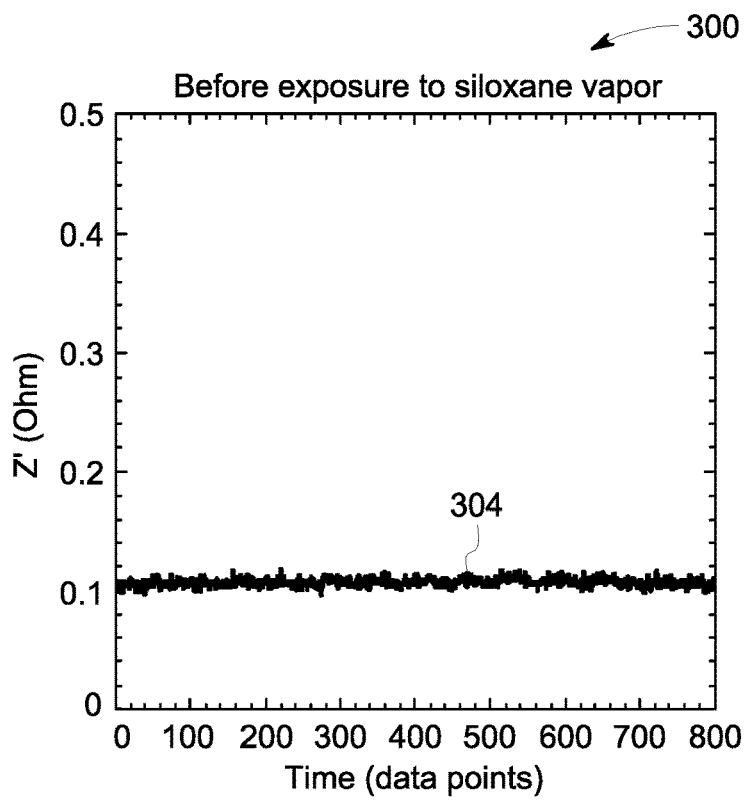
FIG. 4D is a graph depicting an example of a real part of an impedance response pattern of the gas sensor to the ten concentrations of methanol vapor at 12.6 MHz, prior to exposure to the siloxane vapor, in accordance with aspects of the present technique.
Figure 4E:
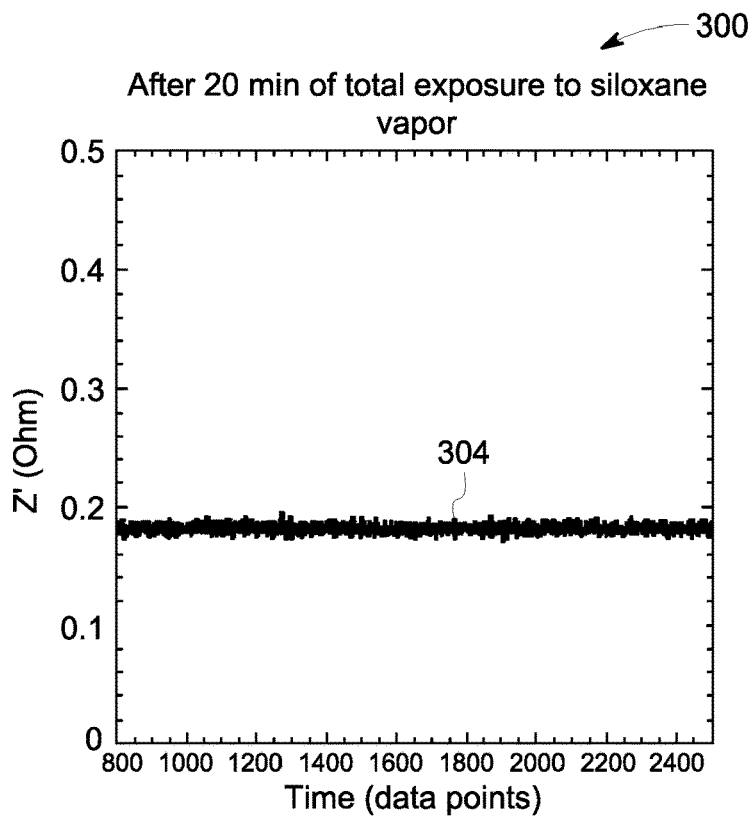
FIG. 4E is a graph depicting an example of a real part of an impedance response pattern of the gas sensor to the ten concentrations of methanol vapor with two replicates at 12.6 MHz, after 20 minutes of exposure to the siloxane vapor, in accordance with aspects of the present technique.
Figure 4F:
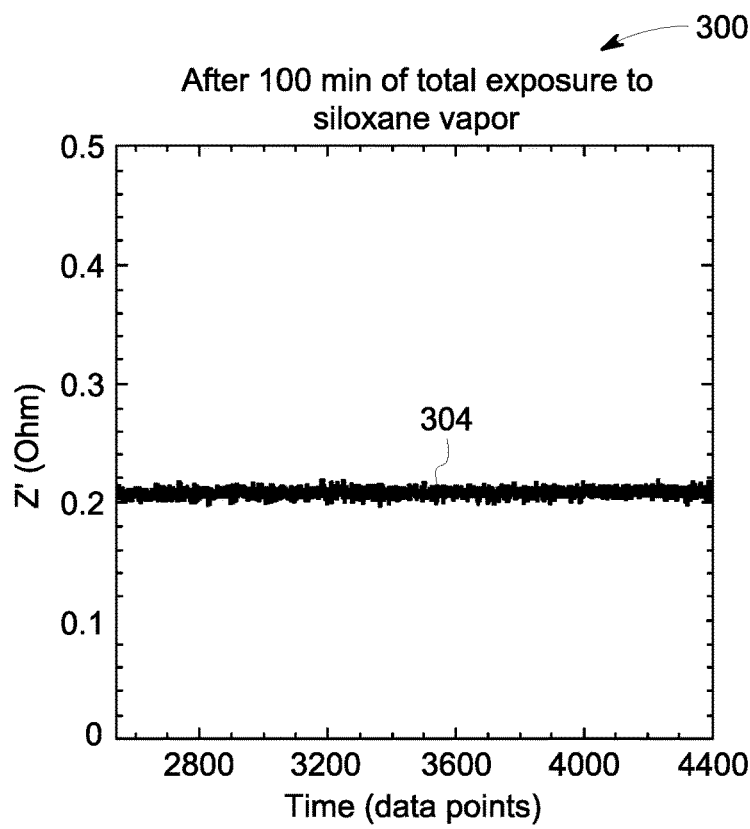
FIG. 4F is a graph depicting an example of a real part of an impedance response pattern of the gas sensor to the ten concentrations of methanol vapor with two replicates at 12.6 MHz, after 100 minutes of exposure to the siloxane vapor, in accordance with aspects of the present technique.

The responses shown in FIGS. 4D-4F represent the real part 304 (first curve 202 in FIG. 3) of the measured impedance at the high frequency shoulder region 206 of the gas sensing material 22 at 12.6 MHz. As shown, at 12.6 MHz, the response of the gas sensing material 22 to methanol vapor was not detectable and/or indiscernible, but the baseline increased as the time of exposure of the gas sensing material 22 to the siloxane vapor increased, indicating that the baseline level changes were related to the sensor poison level changes.

Figure 5A:
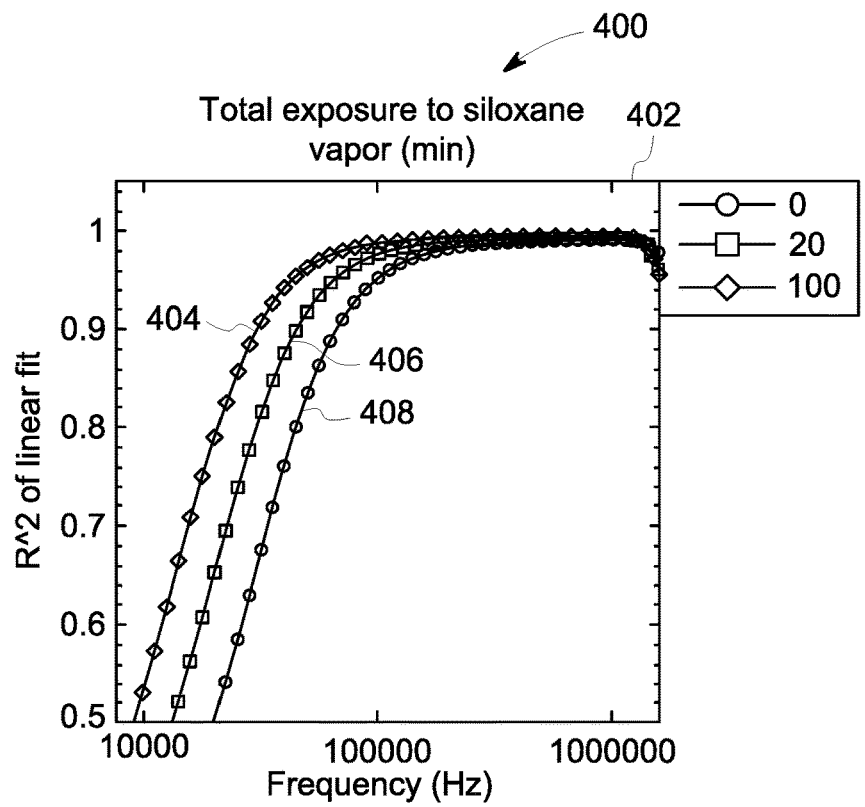
FIG. 5A is a graph depicting coefficients of determination values of the linear fit for the three sensor poisoning levels (i.e., 0, 20, and 100 minutes of exposure to siloxane vapor), in accordance with aspects of the present technique.

To quantify the response linearity of the imaginary part of the measured impedance, linear fits were applied to the responses at all measured frequencies, and coefficients of determination ("$R^2$") values were determined for the three sensor poisoning levels (i.e., 0, 20, and 100 minutes of exposure to siloxane vapor). FIG. 5A is a graph 402 of the three $R^2$ value plots 404, 406, 408 over the measured frequencies. As illustrated, the $R^2$ value for each of the three sensor poisoning levels approach 1.0 as the frequency increases. Further, the $R^2$ value appears to improve slightly as the exposure time to siloxane vapor increases. Additionally, the frequency ranges at which the response is linear overlapped before and after exposure to siloxane vapor. Thus, the dielectric excitation of the gas sensing material 22 appeared to provide a linear response before and after sensor poisoning, which simplifies the calibration of such gas sensors 10. The response may be considered substantially linear if the $R^2$ value exceeds 0.9, 0.95, 0.96, 0.97, 0.98, 0.99, or some other threshold value.

Figure 5B:
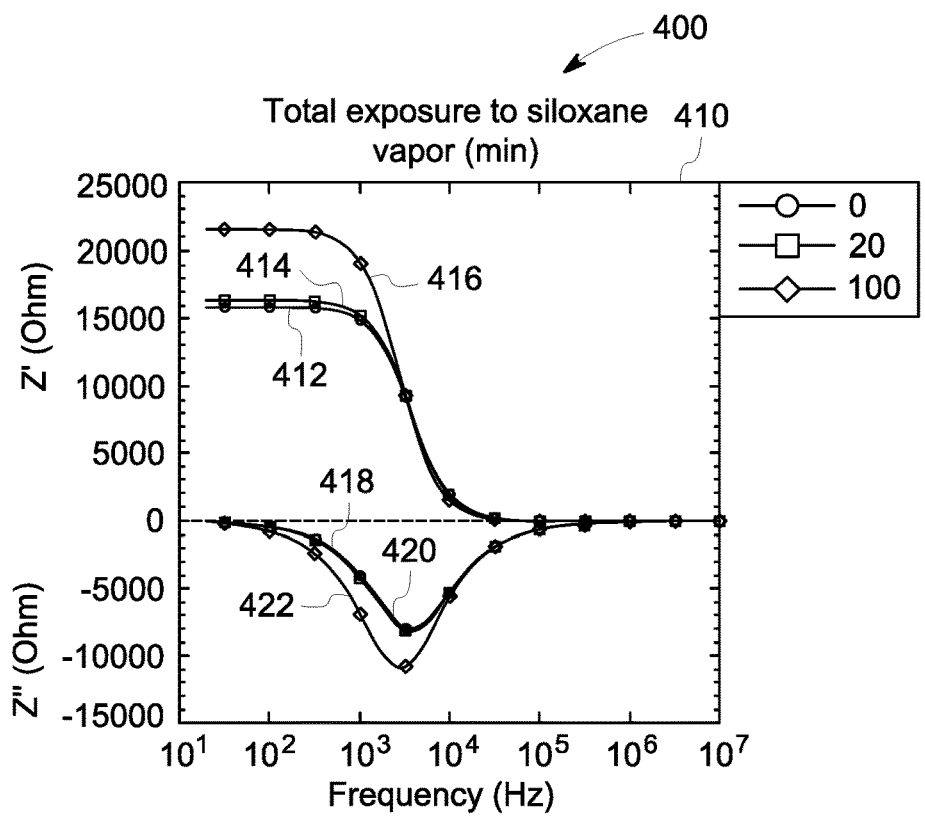
FIG. 5B is a graph depicting impedance spectra for real and imaginary parts of the impedance response before the exposure to the siloxane vapor, after 20 minutes of the exposure to the siloxane vapor, and after 100 minutes of the exposure to the siloxane vapor, in accordance with aspects of the present technique.
Figure 5C:
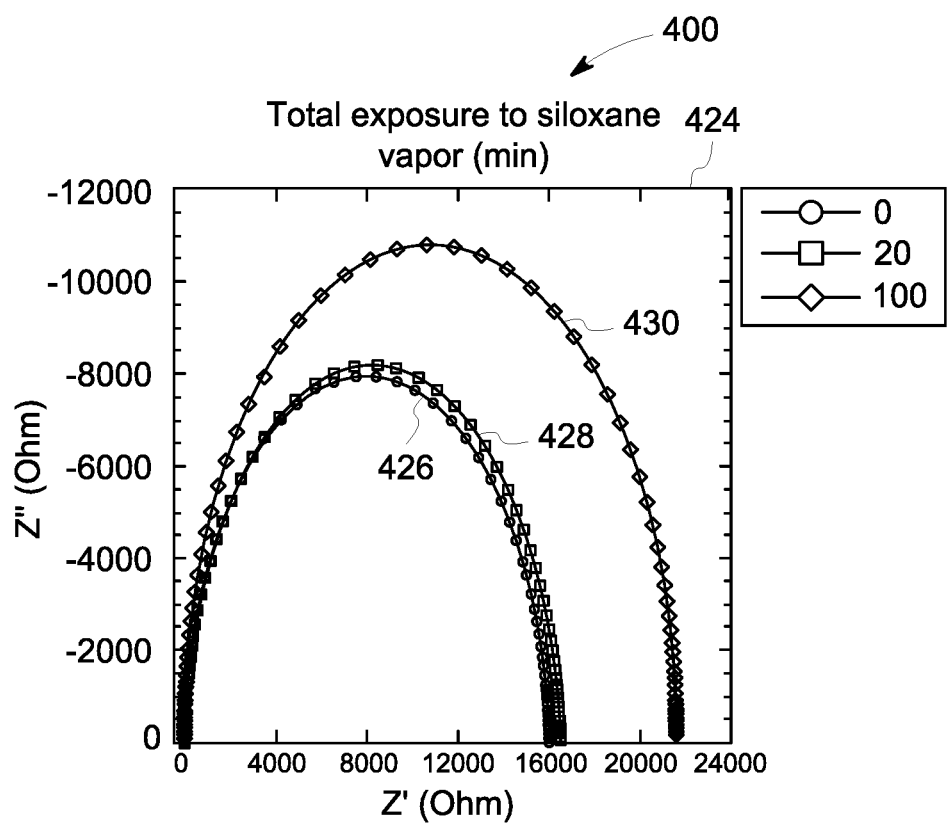
FIG. 5C is a graph depicting Nyquist plots for the real versus imaginary parts of the impedance response before the exposure to the siloxane vapor, after 20 minutes of the exposure to the siloxane vapor, and after 100 minutes of the exposure to the siloxane vapor, in accordance with aspects of the present technique.

FIG. 5B is a graph 410 of the frequency spectra for the real parts of the response Z' before exposure to siloxane vapor 412, after 20 minutes of exposure to siloxane vapor 414, and after 100 minutes of exposure to siloxane vapor 416, and the imaginary parts of the response Z" before exposure to siloxane vapor 418, after 20 minutes of exposure to siloxane vapor 420, and after 100 minutes of exposure to siloxane vapor 422. As shown, after the gas sensing material 22 was exposed to siloxane vapor, the spectra for the real portion of the response increased in value at frequencies at the lower end of the measurement range. Similarly, the spectra for the imaginary portion of the response increased in value as the time of exposure to siloxane vapor increased. FIG. 5C is a graph 424 of Nyquist plots for the real versus imaginary portions of the response before exposure to siloxane vapor 426, after 20 minutes of exposure to siloxane vapor 428, and after 100 minutes of exposure to siloxane vapor 430. As shown, the Nyquist plots 426, 428, 430 have no depression angles, indicating no effects from non-Debye relaxation.

Figure 6:
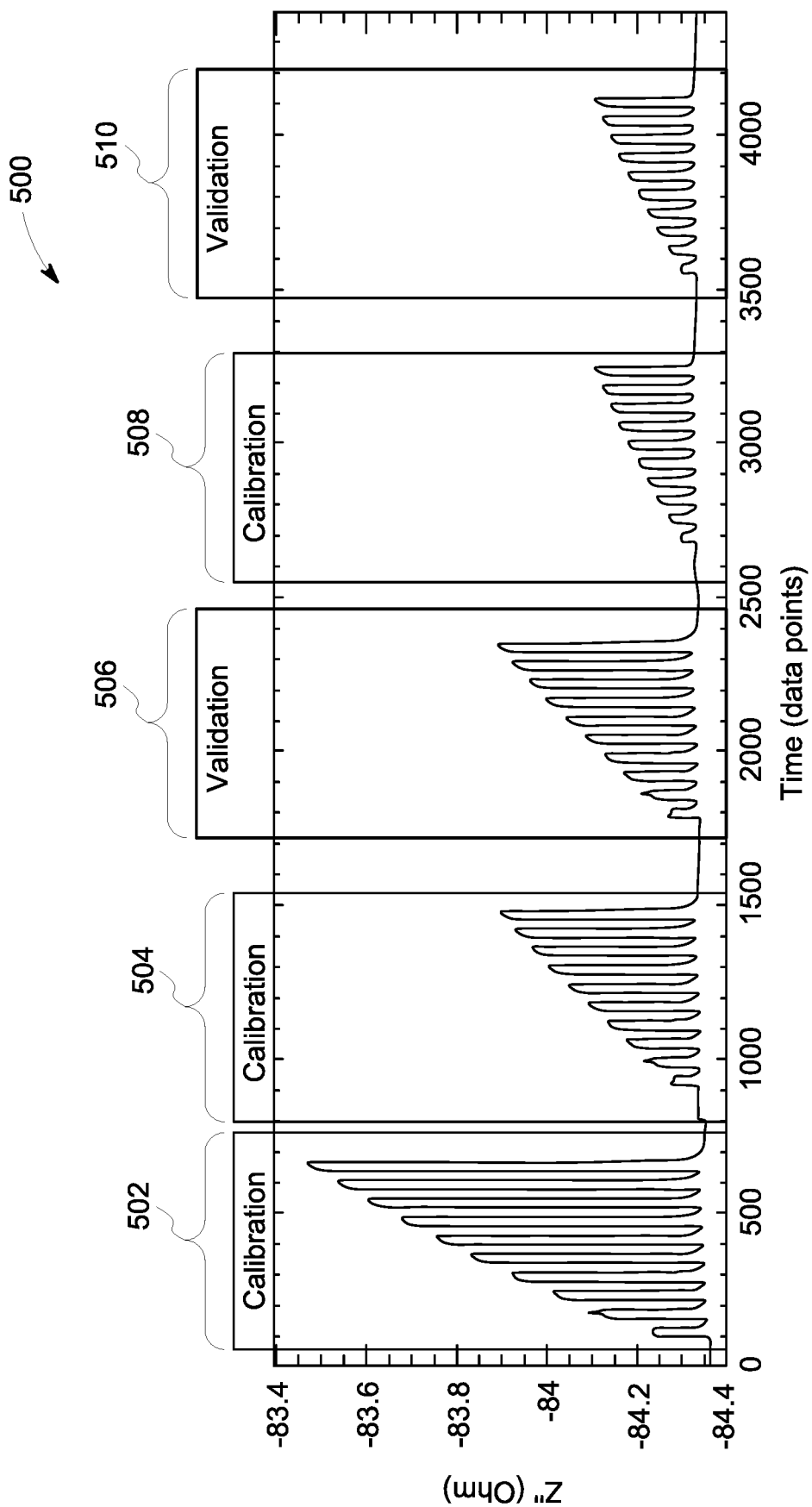
FIG. 6 is a graph depicting the imaginary part of the measured impedance response of the gas sensing material to the dielectric excitation during a calibration and validation test, in accordance with aspects of the present technique.

FIG. 6 is a graph 500 of the imaginary part of the measured response of the gas sensing material 22 to dielectric excitation during a calibration and validation test. In the graph 500 shown in FIG. 6, the horizontal axis represents time while the vertical axis represent the magnitude of the impedance of the imaginary part of the measured response Z". As shown, the graph can be broken up into various phases 502, 504, 506, 508, 510. At phase 502, for calibration, the graph displays the imaginary portion of the response of the gas sensing material 22 to the ten concentrations of methanol vapor at 0.7 MHz before exposure to siloxane vapor. At phase 504, for calibration, the graph displays the imaginary portion of the response of the gas sensing material 22 to the ten concentrations of methanol vapor at 0.7 MHz after 20 minutes of exposure to siloxane vapor. At phase 506, for validation, the graph displays the imaginary portion of the response of the gas sensing material 22 to a second set of exposures to the ten concentrations of methanol vapor at 0.7 MHz after 20 minutes of exposure to siloxane vapor. At phase 508, for calibration, the graph displays the imaginary portion of the response of the gas sensing material 22 to the ten concentrations of methanol vapor at 0.7 MHz after 100 minutes of exposure to siloxane vapor. At phase 510, for validation, the graph displays the imaginary portion of the response of the gas sensing material 22 to a second set of exposures to the ten concentrations of methanol vapor at 0.7 MHz after 100 minutes of exposure to siloxane vapor. A mathematical transfer function was then developed based on the response of the gas sensing material 22 at 0.7 MHz and at 12.6 MHz, such that the sensor poison level of the gas sensor 10 can be determined and the response of the gas sensing material 22 corrected to account for the determined sensor poison level of the gas sensor 10, and thus accurately determine concentrations of various gases within a fluid sample. As an example, the mathematical transfer function may be developed based on a conventional support vector machine regression algorithm.

Figure 7A:
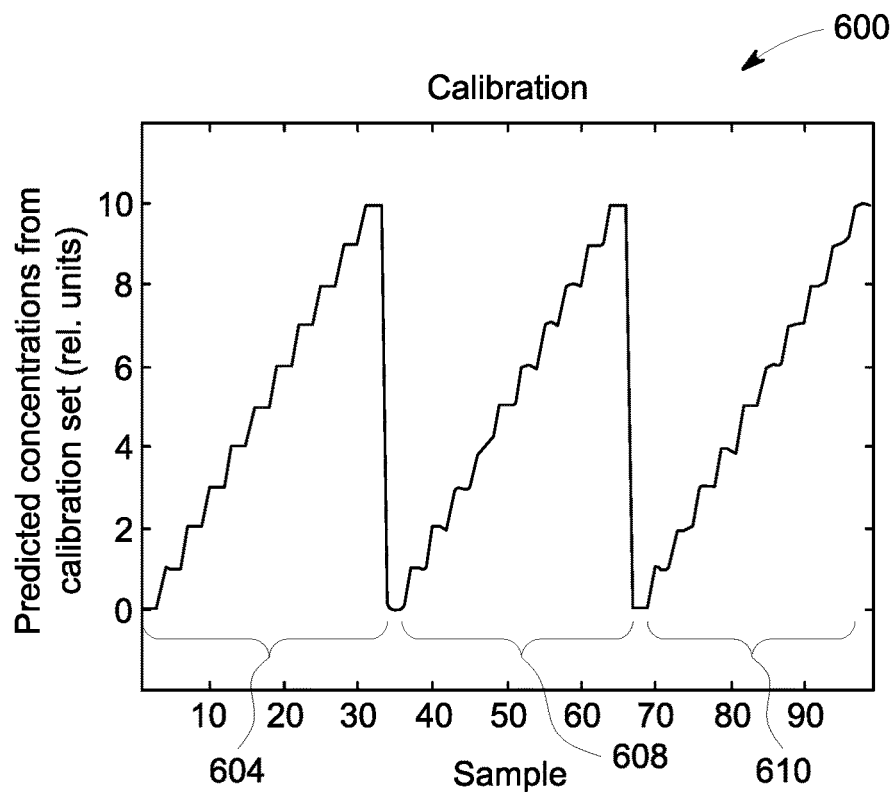
FIG. 7A is a graph depicting predicted concentrations of methanol vapor based on a calibration data set, in accordance with aspects of the present technique.
Figure 7B:
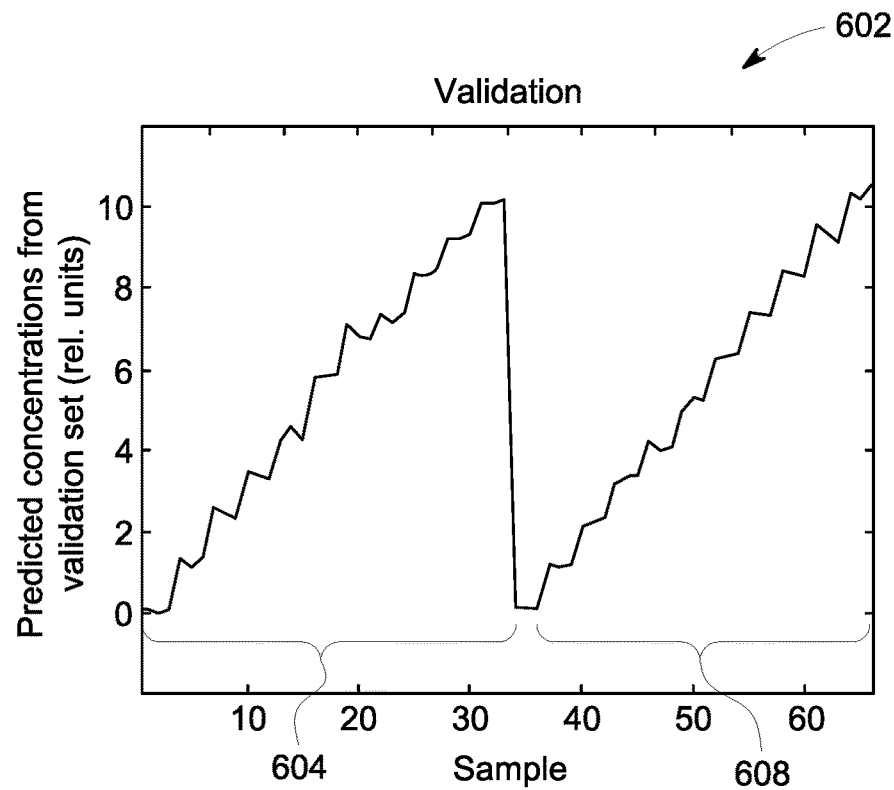
FIG. 7B is a graph depicting predicted concentrations of methanol vapor based on a validation data set, in accordance with aspects of the present technique.

FIGS. 7A and 7B are graphs 600, 602 of predicted concentrations of methanol vapor based on the calibration set (FIG. 7A) and the validation set (FIG. 7B), respectively. As shown, the transfer function was applied to the response data for the various calibration phases 502, 504, 508 shown in FIG. 6 to correct for the sensor poisoning of the gas sensing material 22 (by exposure to siloxane vapor). Accordingly, because the ten concentrations of methanol vapor to which the gas sensor was exposed are known (i.e., 6.25 ppm, 12.50 ppm, 18.75 ppm, 25.00 ppm, 31.25 ppm, 37.50 ppm, 43.75 ppm, 50.00 ppm, 56.25 ppm, and 62.50 ppm), the transfer function was able to predict concentrations based on the calibration data set match the known concentrations. The vertical axis in FIG. 7A depicts predicted concentrations of methanol vapor from the calibration set, where the predicted concentrations are displayed in relative units from 0 to 10 that correspond to actual concentrations from 0 to 62.50 ppm. The transfer function was then applied to the validation data set to predict concentrations of methanol vapor, as shown in FIG. 7B, which can then be compared to the known concentrations of methanol vapor to which the gas sensor was exposed are known (i.e., 6.25 ppm, 12.50 ppm, 18.75 ppm, 25.00 ppm, 31.25 ppm, 37.50 ppm, 43.75 ppm, 50.00 ppm, 56.25 ppm, and 62.50 ppm) to evaluate the transfer function. The vertical axis in FIG. 7B depicts predicted concentrations of methanol vapor from the validation set, where the predicted concentrations are displayed in relative units from 0 to 10 that correspond to actual concentrations from 0 to 62.50 ppm.

Accordingly, these experimental results indicate that a poison level for a gas sensor can be determined based on responses to first and second dielectric excitation at certain first and second respective frequencies. A transfer function, coefficient multiplier, lookup table, model, etc. may then be generated and applied to responses to first and/or second dielectric excitation at certain second and/or second frequencies to correct for sensor poisoning and resolve identities and/or concentrations of gases present in a fluid sample.

Technical effects of this disclosure include enabling correction of a poisoned gas sensor. Using the disclosed techniques, a MOS-based gas sensor can be designed, manufactured, and used to resolve a plurality of gases in a fluid sample even after the sensor has been poisoned. Specifically, the response of the sensor to first and second dielectric excitation at first and second frequencies may be used to determine a poison level of the sensor. The response of the sensor to dielectric excitation at one or more frequencies may then be corrected, based on the determined poison level, to determine identities and/or concentrations of gases present in a fluid sample. Accordingly, by utilizing the presently disclosed techniques, a sensor may continue to be used and output reliable results after poisoning, thus extending the usable life of such gas sensors in environments where sensor poisoning gases may be present. Extending the usable life of gas sensors conserves resources (e.g., time, money, etc.) spent replacing poisoned sensors.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A gas sensor for analysis of one or more gases in a fluid sample, comprising:
 a gas sensing material configured to contact the fluid sample; and
 a measurement circuit operatively coupled to the gas sensing material and configured to:
   provide first and second dielectric excitation of the gas sensing material at first and second respective sets of frequencies while the gas sensing material is in contact with the fluid sample;
   measure responses of the gas sensing material to the first and second dielectric excitation at the first and second respective sets of frequencies while the gas sensing material is in contact with the fluid sample;
   determine, based on the response of the gas sensing material to the first and second dielectric excitation at the first and second respective sets of frequencies, a poison level of the gas sensing material;
   apply, based on the determined poison level and the responses of the gas sensing material to the first and second dielectric excitation at the first and second respective sets of frequencies, a transfer function configured to generate a corrected response that corrects the measured response of the gas sensing material for the poison level of the gas sensing material; and
   output the corrected response.

2. The gas sensor of claim 1, wherein the measurement circuit is configured to determine, based on the responses of the gas sensing material to the first and second dielectric excitation at the first and second respective sets of frequencies, identities, respective concentrations, or a combination thereof, of at least one analyte gas in the fluid sample.

3. The gas sensor of claim 2, wherein the responses of the gas sensing material to the second dielectric excitation are indicative of the poison level, but not the identities and the respective concentrations of the at least one analyte gas in the fluid sample.

4. The gas sensor of claim 1, wherein response linearity to a gas of interest is substantially maintained at a particular frequency of the first set of frequencies, independent of the poison level.

5. The gas sensor of claim 1, wherein each frequency of the first set of frequencies is lower than each frequency of the second set of frequencies.

6. The gas sensor of claim 1, wherein a pre-selected frequency of the first set of frequencies is selected based on the pre-selected frequency being disposed on a shoulder of a dielectric relaxation region of the gas sensing material.

7. The gas sensor of claim 1, wherein the gas sensing material comprises a metal oxide semiconductor (MOS) sensing material.

8. The gas sensor of claim 7, wherein the MOS sensing material is an n-type sensing material, a p-type sensing material, or a composite n-and p-type sensing material.

9. The gas sensor of claim 7, wherein the MOS sensing material is a single-metal oxide, a perovskite oxide with two differently sized cations, or a mixed metal oxide composition.

10. The gas sensor of claim 1, wherein the gas sensor comprises a wearable gas sensor, an ingestible gas sensor, or a tattooed gas sensor, is integrated into a mobile electronic device, is integrated into an unmanned vehicle, or is a part of a wireless sensor network.

11. The gas sensor of claim 1, wherein the poison level is a result of the gas sensing material being exposed to a siloxane vapor.

12. The gas sensor of claim 1, comprising:
a heating element coupled to the gas sensing material and configured to heat the gas sensing material; and
a heating element controller operatively coupled to the heating element and configured to control the heating element to heat the gas sensing material.

13. A method of operating a gas sensor, comprising:
exposing a gas sensing material of the gas sensor to a fluid sample;
providing, via an impedance detector operatively coupled to the gas sensing material, first dielectric excitation of the gas sensing material at a first set of frequencies;
measuring responses of the gas sensing material to the first dielectric excitation at the first set of frequencies while the gas sensing material is in contact with the fluid sample;
providing, via the impedance detector, second dielectric excitation of the gas sensing material at a second set of frequencies;
measuring responses of the gas sensing material to the second dielectric excitation at the second set of frequencies while the gas sensing material in contact with the fluid sample; and
determining, based on the responses of the gas sensing material to the first and second dielectric excitation at the first and second set of frequencies, identities, respective concentrations, or a combination thereof, of at least one analyte gas of the fluid sample, and a sensor poison level of the gas sensing material.

14. The method of claim 13, comprising:
identifying one or more frequencies of the first set of frequencies at which the response of the gas sensing material to the first dielectric excitation is substantially linear; and
applying a transfer function to data collected from the response of the gas sensing material to the first dielectric excitation at the one or more frequencies of the first set of frequencies and to the second dielectric excitation at the one or more frequencies of the second set of frequencies to generate corrected response data that corrects for the sensor poison level.

15. The method of claim 14, wherein the responses of the gas sensing material to the at least one analyte gas are indiscernible at the second set of frequencies.

16. The method of claim 14, wherein the transfer function is based on real and imaginary parts of an impedance spectra at the first and second sets of frequencies.

17. A method of calibrating a gas sensor, comprising:
obtaining first responses of the gas sensor to first dielectric excitation at a first frequency range while the gas sensor is in contact with a range of known concentrations of a gas, wherein the first responses of the gas sensor over the range of known concentrations of the gas are substantially linear;
relating the first responses of the gas sensor to the range of known concentrations of the gas;
computing one or more analytical fit coefficients between the first responses and the range of known concentrations of the gas, wherein the one or more analytical fit coefficients correct for a poison level of the gas sensor;
storing the one or more analytical fit coefficients on an on-board memory, accessible by an on-board processor;
obtaining second responses of the gas sensor to second dielectric excitation at a second frequency range while the gas sensor is in contact with an unknown concentration of the gas; and
determining, based on the second responses of the gas sensor, and the one or more analytical fit coefficients, the unknown concentration of the gas.

18. The method of claim 17, comprising:
providing the first and second dielectric excitation of the gas sensor at the first and second respective frequency ranges while the gas sensing material is in contact with a fluid sample that includes the gas; and
measuring the first and second responses of the gas sensor to the first and second dielectric excitation at the first and second frequency ranges while the gas sensing material is in contact with the fluid sample that includes the gas.

19. The method of claim 17, wherein determining, based on the second responses of the gas sensor, and the one or more analytical fit coefficients, the unknown concentration of the gas comprises applying a transfer function to the second responses of the gas sensor to the second dielectric excitation at the second frequency range, wherein the transfer function is based on the stored one or more analytical fit coefficients and is configured to correct for the poison level of the gas sensor.

20. The method of claim 19, wherein the transfer function is based on real and imaginary parts of an impedance spectra at the first frequency range, the second frequency range, or both.

* * * * *